US007038108B2

(12) United States Patent
Falco et al.

(10) Patent No.: US 7,038,108 B2
(45) Date of Patent: May 2, 2006

(54) POLYNUCLEOTIDE ENCODING LYSYL-TRNA SYNTHETASE FROM ZEA MAYS

(75) Inventors: Saverio C. Falco, Arden, DE (US); Carl R. Simmons, Des Moines, DE (US)

(73) Assignees: E.I. du Pont de Nemours and Company, Wilmington, DE (US); Pioneer Hi-Bred International. Inc., Johnston, IA (US)

( * ) Notice: Subject to any disclaimer, the term of this patent is extended or adjusted under 35 U.S.C. 154(b) by 0 days.

(21) Appl. No.: 09/864,464

(22) Filed: May 24, 2001

(65) Prior Publication Data
US 2003/0018985 A1    Jan. 23, 2003

Related U.S. Application Data

(62) Division of application No. 09/357,251, filed on Jul. 20, 1999, now Pat. No. 6,271,441.

(60) Provisional application No. 60/093,530, filed on Jul. 21, 1998.

(51) Int. Cl.
*C12N 15/82* (2006.01)
*C12N 1/20* (2006.01)
*C12N 15/00* (2006.01)
*A01H 5/00* (2006.01)
*A01H 5/10* (2006.01)

(52) U.S. Cl. ............... 800/278; 435/194; 435/69.1; 435/350; 435/320.1; 435/252.3; 435/325; 435/410; 435/419; 435/183; 435/231; 435/193; 800/295; 536/23.2

(58) Field of Classification Search ............ 536/23.1, 536/23.2, 23.6; 435/320.1, 252.3, 254.11, 435/325, 419, 468, 471; 800/295
See application file for complete search history.

(56) References Cited

U.S. PATENT DOCUMENTS 5,759,833 A * 6/1998 Shiba et al.

OTHER PUBLICATIONS

Giritch et al. A root-specific iron-regulated gene of tomato encodes a lysyl-tRNA-synthetase-like protein. Eur. J. Biochem. (1997) 244(2): 310-317.*
GenBank Accession No. AF125574. Arabidopsis thaliana lysyl-tRNA synthetase mRNA, complete cds. Mar. 3, 1999.*
Genbank Accession No. X94451. L. esculentum mRNA for lysyl-tRNA synthetase. Apr. 8, 1997.*
Terada et al. Functional convergence of two lysyl-tRNA synthetases with unrelated topologies. Nature Structural Biology (2002) 9:257-262.*
Nichols et al. Human iso-leucyl-tRNA synthetase:sequence of the cDNA, alternative mRNA splicing, and the characteristics of an unusually long C-terminal extension. Gene, 1995, vol. 155:299-304.*
GenBank Accession No. U04953, dated Oct. 31, 1995.*
National Center for Biotechnology Information General Identifier No. 135134, Feb. 1, 1996.
Duane W. Martindale et al., "Isolation and Complete Sequence of the Yeast isoleucyl-tRNA Synthetase gene (ILSI)", Curr. Genet. 15(2), 99-106, (1989).
Uwe Englisch et al., Biol. Chem. Hoppe-Seyler, "Structure of the Yeast Isoleucyl-tRNA Synthetase Gene (ILSI)", vol. 368 (8), 971-979 (Aug. 1987).
Brigitte Obermaier et al., "Sequence Analysis of a 78 6 kb Segment of the Left end of Saccharomyces cerevisiae Chromosome II", Yeast, vol. 11:1103-1112 (1995).
National Center for Biotechnology Information General Identifier No. 730870, Nov. 1, 1997.
Kiyotaka Shiba et al., "Human cytoplasmic isoleucyl-tRNA synthetase: Selective divergence of the anticodon-binding domain and acquisition of a new structural unit", Proc. Natl. Acad. Sci. 91 (16), 7435-7439, (Aug. 1994).
National Center for Biotechnology Information General Identifier No. 4504555, Mar. 19, 1999.
Dharam P. Singal et al., "Human Y-box transcription factors: sequences of two new YB-I alleles", Gene 154 (2), 299-300 (1995).

(Continued)

*Primary Examiner*—Ponnathapura N. Achutamurthy
*Assistant Examiner*—Kagnew Gebreyesus

(57) ABSTRACT

This invention relates to isolated nucleic acid fragments encoding aminoacyl-tRNA synthetases and particulary Isoleucyl-, lysyl-, phenylalanyl- and prolyl-tRNA synthetases from *Zea mays*, *Oryza sativa*, *Glycine max* and *Tritium aestivum*. The invention also relates to the construction of a chimeric gene encoding all or a portion of the aminoacyl-tRNA synthetase, in sense or antisense orientation, wherein expression of the chimeric gene results in production of altered levels of the aminoacyl-tRNA synthetase in a transformed host cell.

11 Claims, No Drawings

OTHER PUBLICATIONS

National Center for Biotechnology Information General Identifier No. 4325324, Mar. 3, 1999.

National Center for Biotechnology Information General Identifier No. 3983103, Dec. 9, 1998.

National Center for Biotechnology Information General Identifier No. 172947, Apr. 27, 1993.

Ambaliou Sanni et al., "Structure and Expression of the Genes Encoding the a and B subunits of Yeast Phenylalanyl-tRNA Synthetase", J. Biol. Chem. 263, 15407-15415 (1988).

National Center for Biotechnology Information General Identifier No. 4758294, May 7, 1999.

Radegunde Fett et al., "The Primary Structure of Human Glutaminyl-tRNA Synthetase", J. Biol. Chem. 266(3), 1448-1455 (1991).

Neidhartdt, et al, "Function and Regulation of AminoAcyl-tRNA Synthetases in Prokaryotic and Eukaryotic Cells", Annu. Rev. Microbiology, pp. 215-250, 1975.

Jerzy Zon et al., "Novel Phenylalanine Analogues as Putative Inhibitors of Enzymes Acting on Phenylalanine", Phytochemistry, vol. 27, No. 3 pp. 711-714 (1988).

Donald Heacock et al., "Synthesis and Aminoacyl-tRNA Synthetase Inhibitory Activity of Prolyl Adenylate Analogs", Bioorganic Chemistry 24, 273-289 (1996).

Arnez, John G. et al., "Structural and functional considerations of the aminoacylation reaction," TIBS, Jun. 1997, 22:211-216.

Desogus, Gianluigi et al., "Active Site of Lysyl-tRNA Synthetase: Structural Studies of the Adenylation Reaction," Biochemistry, 2000, vol. 39:8418-8425.

Albert L. Lehninger, et al.; "Principles in Biochemistry with an Extended Discussion of Oxygen-Binding Proteins", 1993, 912-913, Worth Publishers, New York, US.

* cited by examiner

POLYNUCLEOTIDE ENCODING LYSYL-TRNA SYNTHETASE FROM ZEA MAYS

This application is a divisional of application Ser. No. 09/357,251, filed Jul. 20, 1999, now U.S. Pat. No. 6,271,441, which claims the benefit of U.S. Provisional Application No. 60/093,530, filed Jul. 21, 1998.

FIELD OF THE INVENTION

This invention is in the field of plant molecular biology. More specifically, this invention pertains to nucleic acid fragments encoding aminoacyl-tRNA synthetase in plants and seeds.

BACKGROUND OF THE INVENTION

All tRNAs have two functions: to chemically link to a specific amino acid and to recognize a codon in mRNA so that the linked amino acid can be added to a growing peptide chain during protein synthesis. In general there is at least one aminoacyl-tRNA synthetase for each of the twenty amino acids. A specific aminoacyl-tRNA synthetase links an amino acid to the 2' or 3' hydroxyl of the adenosine residue at the 3'-terminus of a tRNA molecule. Once its correct amino acid is attached, a tRNA then recognizes a codon in mRNA, thus delivering its amino acid to the growing polypeptide chain. These enzymatic functions are critical to gene expression (Neidhart et al. (1975) *Annu. Rev. Microbiol.* 29:215–250). Mutations in tRNA synthetases often result in alterations in protein synthesis and in some cases cell death.

Plants like other cellular organisms have aminoacyl-tRNA synthetases. However a complete description of the plant 'complement' of aminoacyl-tRNA synthetases has not been published. It is anticipated that plants will likely have at least forty aminoacyl-tRNA synthetases. Plants have three sites of protein synthesis: the cytoplasm, the mitochondria and the chloroplast. Accordingly, there could be as many as sixty aminoacyl-tRNA synthetases. Based on knowledge of other eukaryotes the cytoplasmic and mitochondrial aminoacyl-tRNA synthetases are expected to be encoded by the same gene. This gene should be nuclearly encoded and produce two alternate products, one with a mitochondrial specific transit peptide, and the other without the mitochondrial targeting signal. The chloroplast is the other site of protein synthesis in plants. Based on a few examples of known plant chloroplast specific aminoacyl-tRNA synthetase genes it appears that these genes are also nuclear encoded. Chloroplast aminoacyl-RNA synthetases would directed to the chloroplast by a transit peptide.

Because of the central role aminoacyl-tRNA synthetases play in protein synthesis any agent that inhibits or disrupts aminoacyl-tRNA synthetase activity is likely to be toxic. Indeed a number of aminoacyl-tRNA synthetase inhibitors (antibiotics and herbicides) are known (Zon et al. (1988) *Phytochemistry* 27(3):711–714 and Heacock et al. (1996) *Bioorganic Chemistry* 24(3):273–289). Thus it may be possible to develop new herbicides that target aminoacyl-tRNA synthetases and engineer aminoacyl-tRNA synthetases that are resistant to such herbicides. Accordingly, the availability of nucleic acid sequences encoding all or a portion of these enzymes would facilitate studies to better understand protein synthesis in plants, provide genetic tools for the manipulation of gene expression, and provide a possible target for herbicides.

SUMMARY OF THE INVENTION

The instant invention relates to isolated nucleic acid fragments encoding aminoacyl-tRNA synthetase. Specifically, this invention concerns an isolated nucleic acid fragment encoding an isoleucyl-tRNA synthetase, lysyl-tRNA synthetase, phenylalanyl-tRNA synthetase or prolyl-tRNA synthetase and an isolated nucleic acid fragment that is substantially similar to an isolated nucleic acid fragment encoding an isoleucyl-tRNA synthetase, lysyl-tRNA synthetase, phenylalanyl-tRNA synthetase or prolyl-tRNA synthetase. In addition, this invention relates to a nucleic acid fragment that is complementary to the nucleic acid fragment encoding isoleucyl-tRNA synthetase, lysyl-tRNA synthetase, phenylalanyl-tRNA synthetase or prolyl-tRNA synthetase.

An additional embodiment of the instant invention pertains to a polypeptide encoding all or a substantial portion of an aminoacyl-tRNA synthetase selected from the group consisting of isoleucyl-tRNA synthetase, lysyl-tRNA synthetase, phenylalanyl-tRNA synthetase and prolyl-tRNA synthetase.

In another embodiment, the instant invention relates to a chimeric gene encoding an isoleucyl-tRNA synthetase, lysyl-tRNA synthetase, phenylalanyl-tRNA synthetase or prolyl-tRNA synthetase, or to a chimeric gene that comprises a nucleic acid fragment that is complementary to a nucleic acid fragment encoding an isoleucyl-tRNA synthetase, lysyl-tRNA synthetase, phenylalanyl-tRNA synthetase or prolyl-tRNA synthetase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an isoleucyl-tRNA synthetase, lysyl-tRNA synthetase, phenylalanyl-tRNA synthetase or prolyl-tRNA synthetase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an isoleucyl-tRNA synthetase, lysyl-tRNA synthetase, phenylalanyl-tRNA synthetase or prolyl-tRNA synthetase in a transformed host cell comprising: a) transforming a host cell with a chimeric gene comprising a nucleic acid fragment encoding an isoleucyl-tRNA synthetase, lysyl-tRNA synthetase, phenylalanyl-tRNA synthetase or prolyl-tRNA synthetase; and b) growing the transformed host cell under conditions that are suitable for expression of the chimeric gene wherein expression of the chimeric gene results in production of altered levels of isoleucyl-tRNA synthetase, lysyl-tRNA synthetase, phenylalanyl-tRNA synthetase or prolyl-tRNA synthetase in the transformed host cell.

An addition embodiment of the instant invention concerns a method for obtaining a nucleic acid fragment encoding all or a substantial portion of an amino acid sequence encoding an isoleucyl-tRNA synthetase, lysyl-tRNA synthetase, phenylalanyl-tRNA synthetase or prolyl-tRNA synthetase.

A further embodiment of the instant invention is a method for evaluating at least one compound for its ability to inhibit the activity of an isoleucyl-tRNA synthetase, lysyl-tRNA synthetase, phenylalanyl-tRNA synthetase or prolyl-tRNA synthetase, the method comprising the steps of: (a) transforming a host cell with a chimeric gene comprising a nucleic acid fragment encoding an isoleucyl-tRNA synthetase, lysyl-tRNA synthetase, phenylalanyl-tRNA synthetase or prolyl-tRNA synthetase, operably linked to suitable regulatory sequences; (b) growing the transformed host cell under conditions that are suitable for expression of the chimeric gene wherein expression of the chimeric gene results in production of isoleucyl-tRNA synthetase, lysyl-tRNA synthetase, phenylalanyl-tRNA synthetase or prolyl-tRNA synthetase in the transformed host cell; (c) optionally purifying the isoleucyl-tRNA synthetase, lysyl-tRNA synthetase, phenylalanyl-tRNA synthetase or prolyl-tRNA synthetase expressed by the transformed host cell; (d) treating the isoleucyl-tRNA synthetase, lysyl-tRNA synthetase, phenylalanyl-tRNA synthetase or prolyl-tRNA synthetase with a compound to be tested; and (e) comparing the activity of the isoleucyl-tRNA synthetase, lysyl-tRNA synthetase, phenylalanyl-tRNA synthetase or prolyl-tRNA synthetase that has been treated with a test compound to the activity of an untreated isoleucyl-tRNA synthetase, lysyl-tRNA synthetase, phenylalanyl-tRNA synthetase or prolyl-tRNA synthetase, thereby selecting compounds with potential for inhibitory activity.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Aminoacyl-tRNA Synthetase

| Protein | Clone Designation | SEQ ID NO: (Nucleotide) | SEQ ID NO: (Amino Acid) |
|---|---|---|---|
| Isoleucyl-tRNA Synthetase | crln.pk0091.d7 | 1 | 2 |
| Isoleucyl-tRNA Synthetase | rls2.pk0006.c10 | 3 | 4 |
| Isoleucyl-tRNA Synthetase | srm.pk0008.f11 | 5 | 6 |
| Isoleucyl-tRNA Synthetase |␣wre1n.pk0003.c2 | 7 | 8 |
| Lysyl-tRNA Synthetase | p0036.cmtah61r | 9 | 10 |
| Lysyl-tRNA Synthetase | rr1.pk0039.e4 | 11 | 12 |
| Lysyl-tRNA Synthetase | sr1.pk0007.f2 | 13 | 14 |
| Lysyl-tRNA Synthetase | wdk2c.pk005.h13 | 15 | 16 |
| Phenylalanyl-tRNA Synthetase | p0097.cqrao90r | 17 | 18 |
| Phenylalanyl-tRNA Synthetase | rlr48.pk0021.h9 | 19 | 20 |
| Phenylalanyl-tRNA Synthetase | src3c.pk024.b22 | 21 | 22 |
| Phenylalanyl-tRNA Synthetase | wr1.pk0153.d9 | 23 | 24 |
| Prolyl-tRNA Synthetase | p0040.cftag.25r | 25 | 26 |

TABLE 1-continued

Aminoacyl-tRNA Synthetase

| Protein | Clone Designation | SEQ ID NO: (Nucleotide) | SEQ ID NO: (Amino Acid) |
|---|---|---|---|
| Prolyl-tRNA Synthetase | Contig composed of: sfl1.pk0067.a5 sr1.pk0023.f4 ssm.pk0022.a2 | 27 | 28 |
| Prolyl-tRNA Synthetase | wr1.pk0032.h7 | 29 | 30 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences nodding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several aminoacyl-tRNA synthetases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other isoleucyl-tRNA synthetase, lysyl-tRNA synthetase, phenylalanyl-tRNA synthetase or prolyl-tRNA synthetase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of aminoacyl-tRNA synthetase activity and gene expression in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aminoacyl-tRNA synthetase. An example of a vector for high level expression of the instant polypeptides in a bacterial host is provided (Example 9).

Additionally, the instant polypeptides can be used as a targets to facilitate design and/or identification of inhibitors of those enzymes that may be useful as herbicides. This is desirable because the polypeptides described herein catalyze various steps in gene expression. Accordingly, inhibition of the activity of one or more of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| crln | Corn root from 7 day seedlings grown in light* | crln.pk0091.d7 |
| p0036 | Corn tassels, early meiosis | p0036.cmtah61r |
| p0097 | Corn V9 whorl section (7 cm) from plant infected four times with european corn borer | p0097.cqrao90r |
| p0040 | Corn tassel: apical meristem > floral transition | p0040.cftag.25r |
| rlr48 | Rice leaf 15 days after germination, 48 hours after infection of strain *Magaporthe grisea* 4360-R-62 (AVR2-YAMO); Resistant | rlr48.pk0021.h9 |
| rls2 | Rice leaf 15 days after germination, 2 hours after infection of strain *Magaporthe grisea* 4360-R-67 (AVR2-YAMO); Susceptible | rls2.pk0006.c10 |
| rr1 | Rice root of two week old developing seedling | rr1.pk0039.e4 |
| sfl1 | Soybean immature flower | sfl1.pk0067.a5 |
| src3c | Soybean 8 day old root inoculated with eggs of cyst nematode *Heterodera glycinis* (Race 14) for 4 days | src3c.pk024.b22 |
| sr1 | Soybean root | sr1.pk0007.f2 sr1.pk0023.f4 |
| srm | Soybean root meristem | srm.pk0008.f11 |
| ssm | Soybean shoot meristem | ssm.pk0022.a2 |
| wdk2c | Wheat developing kernel, 7 days after anthesis | wdk2c.pk005.h13 |
| wr1 | Wheat root from 7 day old seedling | wr1.pk0032.h7 wr1.pk0153.d9 |
| wre1n | Wheat root from 7 day old etiolated seedling* | wre1n.pk0003.c2 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH 10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding aminoacyl-tRNA synthetases were identified by conducting BLAST (Basic Local Alignment Search Tool; Altschul et al. (1993) *J. Mol Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Isoleucyl-tRNA Synthetase

The BLASTX search using the EST sequences from clones listed in Table 3 revealed similarity of the polypeptides encoded by the cDNAs to isoleucyl-tRNA synthetase from *Saccharomyces cerevisiae* (NCBI Identifier No. gi 135134), *Homo sapiens* (NCBI Identifier No. gi 730870) and *Homo sapiens* (NCBI Identifier No. gi 4504555). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Saccharomyces cerevisiae* and *Homo sapiens* Isoleucyl-tRNA Synthetase

| Clone | Status | BLAST pLog Score |
|---|---|---|
| crln.pk0091.d7 | FIS | 55.40 (gi 135134) |
| rls2.pk0006.c10 | EST | 28.52 (gi 135134) |
| srm.pk0008.f11 | EST | 49.52 (gi 730870) |
| wre1n.pk0003.c2 | FIS | 55.05 (gi 4504555) |

The data in Table 4 represents a calculation of the percent identity of the amino acid sequences set forth in SEQ ID NOs:2, 4, 6 and 8 and the *Saccharomyces cerevisiae* and *Homo sapiens* sequences (SEQ ID NOs:31, 32 and 33).

TABLE 4

Percent Identity of Amino Acid Sequences Deduced From the Nucleotide Sequences of cDNA Clones Encoding Polypeptides Homologous to *Saccharomyces cerevisiae* and *Homo sapiens* Isoleucyl-tRNA Synthetase

| SEQ ID NO. | Percent Identity to |
|---|---|
| 2 | 58% (gi 135134) |
| 4 | 68% (gi 135134) |
| 6 | 58% (gi 730870) |
| 8 | 53% (gi 4504555) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an isoleucyl-tRNA synthetase. These sequences represent the first corn, rice, soybean and wheat sequences encoding isoleucyl-tRNA synthetase.

Example 4

Characterization of cDNA Clones Encoding Lysyl-tRNA Synthetase

The BLASTX search using the EST sequences from clones listed in Table 5 revealed similarity of the polypeptides encoded by the cDNAs to lysyl-tRNA synthetase from *Arabidopsis thaliana* (NCBI Identifier No. gi 4325324). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to *Arabidopsis thaliana* Lysyl-tRNA Synthetase

| Clone | Status | BLAST pLog Score to gi 4325324 |
|---|---|---|
| p0036.cmtah61r | FIS | >254.00 |
| rr1.pk0039.e4 | EST | 92.15 |
| sr1.pk0007.f2 | FIS | >254.00 |
| wdk2c.pk005.h13 | FIS | 65.30 |

The data in Table 6 represents a calculation of the percent identity of the amino acid sequences set forth in SEQ ID NOs:10, 12, 14, and 16 and the *Arabidopsis thaliana* sequence (SEQ ID NO:34).

TABLE 6

Percent Identity of Amino Acid Sequences Deduced From the
Nucleotide Sequences of cDNA Clones Encoding Polypeptides
Homologous to *Arabidopsis thaliana* Lysyl-tRNA Synthetase

| SEQ ID NO. | Percent Identity to gi 4325324 |
| --- | --- |
| 10 | 68% |
| 12 | 85% |
| 14 | 73% |
| 16 | 85% |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a lysyl-tRNA synthetase. These sequences represent the first corn, rice, soybean and wheat sequences encoding lysyl-tRNA Synthetase.

Example 5

Characterization of cDNA Clones Encoding Phenylalanyl-tRNA Synthetase

The BLASTX search using the EST sequences from clones listed in Table 7 revealed similarity of the polypeptides encoded by the cDNAs to phenylalanyl-tRNA synthetase from *Homo sapiens* (NCBI Identifier No. gi 3983103) and *Saccharomyces cerevisiae* (NCBI Identifier No. gi 172947). Shown in Table 7 are the BLAST results for individual ESTs ("EST"), the sequences of the entire cDNA inserts comprising the indicated cDNA clones ("FIS"), or contigs assembled from two or more ESTs ("Contig"):

TABLE 7

BLAST Results for Sequences Encoding Polypeptides
Homologous to *Homo sapiens* and *Saccharomyces
cerevisiae* Phenylalanyl-tRNA Synthetase

| Clone | Status | BLAST pLog Score |
| --- | --- | --- |
| p0097.cqrao90r | FIS | 95.15 (gi 3983103) |
| rlr48.pk0021.h9 | FIS | 82.00 (gi 172947) |
| src3c.pk024.b22 | EST | 27.70 (gi 172947) |
| wr1.pk0153.d9 | EST | 101.00 (gi 172947) |

The data in Table 8 represents a calculation of the percent identity of the amino acid sequences set forth in SEQ ID NOs:18, 20, 22 and 24 and the *Homo sapiens* and *Saccharomyces cerevisiae* sequences (SEQ ID NOs:35 and 36 respectively).

TABLE 8

Percent Identity of Amino Acid Sequences Deduced From the
Nucleotide Sequences of cDNA Clones Encoding Polypeptides
Homologous to *Homo sapiens* and *Saccharomyces cerevisiae*
Phenylalanyl-tRNA Synthetase

| SEQ ID NO. | Percent Identity to |
| --- | --- |
| 18 | 38% (gi 3983103) |
| 20 | 57% (gi 172947) |
| 22 | 41% (gi 172947) |
| 24 | 58% (gi 172947) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a phenylalanyl-tRNA synthetase. These sequences represent the first corn, rice, soybean and wheat sequences encoding phenylalanyl-tRNA synthetase.

Example 6

Characterization of cDNA Clones Encoding Prolyl-tRNA Synthetase

The BLASTX search using the EST sequences from clones listed in Table 9 revealed similarity of the polypeptides encoded by the cDNAs to prolyl-tRNA synthetase from *Homo sapiens* (NCBI Identifier No. gi 4758294). Shown in Table 9 are the BLAST results for individual ESTs ("EST"), the sequences of the entire cDNA inserts comprising the indicated cDNA clones ("FIS"), or contigs assembled from two or more ESTs ("Contig"):

TABLE 9

BLAST Results for Sequences Encoding Polypeptides
Homologous to *Homo sapiens* Prolyl-tRNA Synthetase

| Clone | Status | BLAST pLog Score |
| --- | --- | --- |
| p0040.cftag.25r | FIS | 162.00 |
| Contig composed of: sfl1.pk0067.a5 sr1.pk0023.f4 ssm.pk0022.a2 | Contig | 68.15 |
| wr1.pk0032.h7 | EST | 51.70 |

The data in Table 10 represents a calculation of the percent identity of the amino acid sequences set forth in SEQ ID NOs:26, 28 and 30 and the *Homo sapiens* sequence (SEQ ID NO:37).

TABLE 10

Percent Identity of Amino Acid Sequences Deduced From the Nucleotide Sequences of cDNA Clones Encoding Polypeptides Homologous to *Homo sapiens* Prolyl-tRNA Synthetase

| SEQ ID NO. | Percent Identity to |
|---|---|
| 26 | 49% |
| 28 | 64% |
| 30 | 63% |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a prolyl-tRNA synthetase. These sequences represent the first corn, soybean and wheat sequences encoding prolyl-tRNA synthetase.

Example 7

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 10

Evaluating Compounds for Their Ability to Inhibit the Activity of Aminoacyl-tRNA Synthetase The polypeptides described herein may be produced using any number of methods known to those skilled in the art. Such methods include, but are not limited to, expression in bacteria as described in Example 9, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for aminoacyl-tRNA synthetases are presented by Zon et al. (1988) *Phytochemistry* 27(3):711–714 and Heacock et al. (1996) *Bioorganic Chemistry* 24(3): 273–289.

What is claimed is:

1. An isolated polynucleotide comprising:
   (a) a nucleotide sequence encoding a polypeptide having lysyl-tRNA synthetase activity, wherein the polypeptide has an amino acid sequence of at least 90% sequence identity, based on the Clustal alignment method, when compared to SEQ ID NO:10; or
   (b) a full-length complement of the nucleotide sequence of (a).
2. The polynucleotide of claim 1, wherein the polypeptide has an amino acid sequence of at least 95% sequence identity, based on the Clustal alignment method, when compared to SEQ ID NO:10.
3. The polynucleotide of claim 1, wherein the nucleotide sequence comprises SEQ ID NO:9.
4. The polynucleotide of claim 1, wherein the amino acid sequence of the polypeptide comprises SEQ ID NO:10.
5. A chimeric gene comprising a polynucleotide of claim 1, operably linked to a regulatory sequence.
6. A vector comprising a polynucleotide of claim 1.
7. A method for transforming a cell comprising transforming a cell with a polynucleotide of claim 1.
8. A cell comprising a chimeric gene of claim 5.
9. A method for producing a plant comprising transforming a plant cell with a chimeric gene of claim 5, and regenerating a plant from the transformed plant cell.
10. A plant comprising a chimeric gene of claim 5.
11. A seed comprising a chimeric gene of claim 5.

* * * * *

SEQUENCE LISTING

<160> NUMBER OF SEQ ID NOS: 37

<210> SEQ ID NO 1
<211> LENGTH: 528
<212> TYPE: DNA
<213> ORGANISM: Zea mays

<400> SEQUENCE: 1
gcacgaggtg aacaaggaga tggcctcata ccgtttatac actgtcgtac ccagactcct    60

-continued

```
tggtctcatt gacagcacaa caaactggta cattcgattc aaccgaaagc gactcaaggg      120
agagaacggc cttgacgata cccttcatgc cctaaacacc cttttttgagg ttctgttcac     180 tttgtgccgt ggactggcac cttttacccc tttccttact gacaacatct acctcaagct      240
tctacctcac attcctaagg agctgcaaag tgcagatccc cgaagcgtgc acttcctgcc      300
attccccgat gttcgcgaag agctgttcga tgaagaggtg gagcgacgtg ttggtcgcat      360
gcagcgtgtc attgaacttg ctcgtgtatc gcgtgaacgt cgcgccattg gtctcaagca     420
gcctctcaag acactggtgg tcattcactc cgatcctcaa tatcttgagg atgtcaagtc      480
ccttgagaag tatatcagcg aagagttgaa tgtgcgagac ctcgtgct                   528
```

<210> SEQ ID NO 2
<211> LENGTH: 175
<212> TYPE: PRT
<213> ORGANISM: Zea mays

<400> SEQUENCE: 2

```
His Glu Val Asn Lys Glu Met Ala Ser Tyr Arg Leu Tyr Thr Val Val
  1               5                  10                  15

Pro Arg Leu Leu Gly Leu Ile Asp Ser Thr Thr Asn Trp Tyr Ile Arg
             20                  25                  30

Phe Asn Arg Lys Arg Leu Lys Gly Glu Asn Gly Leu Asp Asp Thr Leu
         35                  40                  45

His Ala Leu Asn Thr Leu Phe Glu Val Leu Phe Thr Leu Cys Arg Gly
     50                  55                  60

Leu Ala Pro Phe Thr Pro Phe Leu Thr Asp Asn Ile Tyr Leu Lys Leu
 65                  70                  75                  80

Leu Pro His Ile Pro Lys Glu Leu Gln Ser Ala Asp Pro Arg Ser Val
                 85                  90                  95

His Phe Leu Pro Phe Pro Asp Val Arg Glu Glu Leu Phe Asp Glu Glu
            100                 105                 110

Val Glu Arg Arg Val Gly Arg Met Gln Arg Val Ile Glu Leu Ala Arg
        115                 120                 125

Val Ser Arg Glu Arg Arg Ala Ile Gly Leu Lys Gln Pro Leu Lys Thr
    130                 135                 140

Leu Val Val Ile His Ser Asp Pro Gln Tyr Leu Glu Asp Val Lys Ser
145                 150                 155                 160

Leu Glu Lys Tyr Ile Ser Glu Glu Leu Asn Val Arg Asp Leu Val
                165                 170                 175
```

<210> SEQ ID NO 3
<211> LENGTH: 451
<212> TYPE: DNA
<213> ORGANISM: Oryza sativa
<220> FEATURE:
<221> NAME/KEY: unsure
<222> LOCATION: (386)
<223> OTHER INFORMATION: n=a,c,g or t
<220> FEATURE:
<223> OTHER INFORMATION: n=a,c,g or t
<220> FEATURE:
<221> NAME/KEY: unsure
<222> LOCATION: (417)
<223> OTHER INFORMATION: n=a,c,g or t
<220> FEATURE:
<221> NAME/KEY: unsure
<222> LOCATION: (443)
<223> OTHER INFORMATION: n=a,c,g or t
<220> FEATURE:
<221> NAME/KEY: unsure
<222> LOCATION: (449)

```
<223> OTHER INFORMATION: n=a,c,g or t

<400> SEQUENCE: 3 cttcccctc tcttgttcca agcccctcct cccttaccc cccgccgcc gccgccgccg      60 ccgcctcatc acccgaaacc ctagccccat tcgccgcggt cgccgcctca cccgaaaccc    120
tagccccatt cgccgccggg gtcgcggcct caggagcgga ggccatggag acgtctgcg    180 aggggaagga cttctccttc cccgcggagg aggagcgcgt gctcaagctg tggtcggagc    240
tcgacgcctt ccacgagcag ctccgccgca cgaagggcgg cgaggagttc atcttctacg    300
acgggccccc gttcgccacc ggcctcccgc actatggcca catcctcgcg ggcacaatca    360
aggacgtggt cacccgccac cagtcnatgc gcggccgcca cgtctcccgc cgcttcnggt    420
gggactgcca tggctccccg tcnagttcna t                                    451

<210> SEQ ID NO 4
<211> LENGTH: 83
<212> TYPE: PRT
<213> ORGANISM: Oryza sativa
<220> FEATURE:
<221> NAME/KEY: UNSURE
<222> LOCATION: (76)
<223> OTHER INFORMATION: Xaa = ANY AMINO ACID

<400> SEQUENCE: 4

Phe Ser Phe Pro Ala Glu Glu Glu Arg Val Leu Lys Leu Trp Ser Glu
 1               5                  10                  15

Leu Asp Ala Phe His Glu Gln Leu Arg Arg Thr Lys Gly Gly Glu Glu
            20                  25                  30

Phe Ile Phe Tyr Asp Gly Pro Pro Phe Ala Thr Gly Leu Pro His Tyr
        35                  40                  45

Gly His Ile Leu Ala Gly Thr Ile Lys Asp Val Val Thr Arg His Gln
    50                  55                  60

Ser Met Arg Gly Arg His Val Ser Arg Arg Phe Xaa Trp Asp Cys His
65                  70                  75                  80

Gly Ser Pro

<210> SEQ ID NO 5
<211> LENGTH: 575
<212> TYPE: DNA
<213> ORGANISM: Glycine max
<220> FEATURE:
<221> NAME/KEY: unsure
<222> LOCATION: (21)
<223> OTHER INFORMATION: n=a,c,g or t
<220> FEATURE:
<221> NAME/KEY: unsure
<222> LOCATION: (219)
<223> OTHER INFORMATION: n=a,c,g or t
<220> FEATURE:
<221> NAME/KEY: unsure
<222> LOCATION: (500)
<223> OTHER INFORMATION: n=a,c,g or t
<220> FEATURE:
<221> NAME/KEY: unsure
<222> LOCATION: (525)
<223> OTHER INFORMATION: n=a,c,g or t
<220> FEATURE:
<221> NAME/KEY: unsure
<222> LOCATION: (564)
<223> OTHER INFORMATION: n=a,c,g or t

<400> SEQUENCE: 5
taccttatca actcacctgt ngtgcgtgct gagccacttc gtttcaagaa agaaggagtt     60
```

```
tatggtgttg ttagggatgt tttcctccct tggtataatg catatcggtt ccttgttcaa      120
aatgcaaaga gggttgaagt tgaaggtcta gcacctttg ttccctttga tcaggccaca       180
cttctgaact caacgaatgt tcttgatcaa tggattaant cagccaccca aagccttatt      240
cattttgtcc gacaagaaat ggatggttat cgcctttaca cagtggttcc ttaccttctg      300
aagtttcttg ataaccttac aaatatttat gtaaggttca atcgtaagag acttaaaggt      360
cgttctgggg aagaagactg caggatagca ctatcaactc tttaccatgt gcttttgtta      420
tcctgtaaag tgatggctcc ttttacacct ttcttcactg aggtgctcta tcaaaatatg      480
cgaaaagttt ctaatggtcn gagggaagcg tacactattg cggtnttcct ccagaagaag      540
gaggaggggg gacgactttt gcgngtgttt ttgga                                 575
```

<210> SEQ ID NO 6
<211> LENGTH: 106
<212> TYPE: PRT
<213> ORGANISM: Glycine max
<220> FEATURE:
<221> NAME/KEY: UNSURE
<222> LOCATION: (18)
<223> OTHER INFORMATION: Xaa = ANY AMINO ACID

<400> SEQUENCE: 6

```
Phe Asp Gln Ala Thr Leu Leu Asn Ser Thr Asn Val Leu Asp Gln Trp
  1               5                  10                  15

Ile Xaa Ser Ala Thr Gln Ser Leu Ile His Phe Val Arg Gln Glu Met
                 20                  25                  30

Asp Gly Tyr Arg Leu Tyr Thr Val Val Pro Tyr Leu Leu Lys Phe Leu
             35                  40                  45

Asp Asn Leu Thr Asn Ile Tyr Val Arg Phe Asn Arg Lys Arg Leu Lys
         50                  55                  60

Gly Arg Ser Gly Glu Glu Asp Cys Arg Ile Ala Leu Ser Thr Leu Tyr
 65                  70                  75                  80

His Val Leu Leu Leu Ser Cys Lys Val Met Ala Pro Phe Thr Pro Phe
                 85                  90                  95

Phe Thr Glu Val Leu Tyr Gln Asn Met Arg
                100                 105
```

<210> SEQ ID NO 7
<211> LENGTH: 572
<212> TYPE: DNA
<213> ORGANISM: Triticum aestivum

<400> SEQUENCE: 7

```
gcacgagctt tagggtgatt gccgataact atgtgactga tgatagtgga accggtgttg      60
tccattgtgc tcctgcattt ggtgaagatg atcatcgcgt ttgccttagt gctggaatta     120
ttgaggctag tggacttgtt gtcgctgttg atgatgatgg tcacttcatt gagaagatat     180
ctcagttcaa agggcgacat gtcaaagagg ctgacaagga tatcatcaat gctgttaagg     240
ataaaggaag acttgttagc aagggagca ttgagcactc ttatccgtat tgttggcgct      300
cgggcactcc tcttatttac cgggctgttc caagctggtt tatcaaggtt gaaaagatca     360
gggatcagtt actagaatgc aacaaggaga cctactgggt tccagattat gtcaaggaaa     420
agagattcca taactggcta gaaggtgcta gggactgggc tgttagcaga agtagattct     480
gggatactcc acttccagtg tggatcagcc aagatggtga agaaaaaaaa aaaaaaaaa      540 aaaaaaaaa aaagaaaaaa aaaaaaaaa aa                                     572
```

<210> SEQ ID NO 8
<211> LENGTH: 173
<212> TYPE: PRT
<213> ORGANISM: Triticum aestivum

<400> SEQUENCE: 8

```
Thr Ser Phe Arg Val Ile Ala Asp Asn Tyr Val Thr Asp Asp Ser Gly
 1               5                  10                  15
Thr Gly Val Val His Cys Ala Pro Ala Phe Gly Glu Asp Asp His Arg
            20                  25                  30
Val Cys Leu Ser Ala Gly Ile Ile Glu Ala Ser Gly Leu Val Val Ala
        35                  40                  45
Val Asp Asp Gly His Phe Ile Glu Lys Ile Ser Gln Phe Lys Gly
    50                  55                  60
Arg His Val Lys Glu Ala Asp Lys Asp Ile Ile Asn Ala Val Lys Asp
 65                  70                  75                  80
Lys Gly Arg Leu Val Ser Lys Gly Ser Ile Glu His Ser Tyr Pro Tyr
                85                  90                  95
Cys Trp Arg Ser Gly Thr Pro Leu Ile Tyr Arg Ala Val Pro Ser Trp
            100                 105                 110
Phe Ile Lys Val Glu Lys Ile Arg Asp Gln Leu Leu Glu Cys Asn Lys
        115                 120                 125
Glu Thr Tyr Trp Val Pro Asp Tyr Val Lys Glu Lys Arg Phe His Asn
    130                 135                 140
Trp Leu Glu Gly Ala Arg Asp Trp Ala Val Ser Arg Ser Arg Phe Trp
145                 150                 155                 160
Gly Thr Pro Leu Pro Val Trp Ile Ser Gln Asp Gly Glu
                165                 170
```

<210> SEQ ID NO 9
<211> LENGTH: 2175
<212> TYPE: DNA
<213> ORGANISM: Zea mays

<400> SEQUENCE: 9

| | | | | |
|---|---|---|---|---|
| acttgagcct | ccaccttctc | cgcgtctcac | cttcttctcc | gttctccttc cgctcccctc | 60 |
| ttcacaacga | agccctagtg | tcccgcgaca | tggcatctgg | tctggaggag aaactcgcgg | 120 |
| ggctctcaac | gggcggcgac | gggcaaaatc | ctccgccggc | gggtgagggc ggagaggagc | 180 |
| cgcagctctc | gaagaatgcg | aagaagagag | aggagaagag | gaagaagctg aagaggagc | 240 |
| ggaggctcaa | ggaggaagag | aagaagaaca | aggctgcggc | tgccagtgga aaacctcaga | 300 |
| aggcatctgc | tgctgacgat | gatgacatgg | atcccactca | atactatgag aataggctca | 360 |
| aggctcttga | ttcactgaag | gccacaggtg | taaacccta | tccccataag ttcccggttg | 420 |
| gcatttctgt | acccgaatac | attgagaagt | acaggacctt | gagcgagggg gagaagctta | 480 |
| cagatgtggc | agagtgttta | gctgggagga | tcatgaacaa | gagaacatcg tcgtcgaagc | 540 |
| tattcttta | tgatctttat | ggtggtggca | tgaaggttca | agtgatggct gatgccagga | 600 |
| cctcagagtt | ggatgaagct | gaattttcta | agtaccactc | aggtgtgaag cgaggtgata | 660 |
| ttgttggcat | atgtggatat | ccaggaaaaa | gcaaccgagg | ggagcttagt gtatttccaa | 720 |
| agagatttgt | cgtcctctct | ccatgtcttc | atatgatgcc | tcgacagaag ggtgaaggaa | 780 |
| gtgcagtgcc | tgtaccgtgg | actccaggaa | tgggtaggaa | catcgaaaat tatgttttga | 840 |
| gggaccagga | aactcggtat | cgtcaaaggt | atcttgatct | tatggtaaac catgaagtga | 900 |

-continued

```
ggcacatctt caagacacga tctaaaattg tctcatttat ccgaaagttt cttgatgacc    960
gtgaattttt ggaggtggag actccgatga tgaacatgat tgctggtgga gcagctgcaa   1020
ggccttttgt tacacatcac aatgaattaa acatgcggct ttttatgcgc attgctcctg   1080
aattatatct gaaggaactg gttgttggtg gattggaccg tgtttatgaa attggaaagc   1140
aattcaggaa tgaaggaatt gatttaacac acaatcctga attcacaact tgtgaatttt   1200
atatggcgta tgcagattat aatgatttga tggagcttac tgaaaccatg ttgtcaggca   1260
tggttaagga cctgacaggt ggctataaga taaaatatca tgcaaatgga gttactaacc   1320
ccccaataga aattgatttc acgcctccct tcagaaggat agatatgatt aaagatttgg   1380
aggctatggc caatctcagt ataccaaaag atctatcaag tgatgaagcg aatcgttatt   1440
tgatagaagc atgtgtgaag tatgatgtga aatgtccacc tccccaaacg catcgcggt    1500 tgcttgacaa gttggttggc catttcttgg aggagacatg tgtgaatcca acatttatca   1560
tcaatcatcc agagataatg agtccattag caaagtggca taggtcccga cctggattga   1620
ctgagaggtt cgagttgttt gttaacaaac atgaggtgtg caacgcatac acagagttga   1680
acgatcctgt tgtgcagagg caacggtttg aggaacaact aaaggaccgt caatctggtg   1740
atgacgaagc tatggctttg gacgaaacat tctgtactgc ccttgagtat ggtttggcac   1800
caacaggtgg ttggggcttg ggaattgatc gcctcacgat gttgctaaca gattctcaga   1860
acattaagga agtacttcta ttcccggcta tgaagcctca agagtagtaa tccacagcca   1920
aaagccacaa aaggctcaaa gcaaacatga tgctacatag gctggaggat acatcaaagt   1980
tggacctgtt gtgaattata cttatttttg ctcttgtgcg tgcgaggttt ccatttttca   2040
ttatttgtat ttcccagcag acagttatta actaaatact gtaacgtcac agtaagttca   2100
gtttaacttc aaacattgta gttttgagga gattgcaaat atttcgggtc aatgcaattg   2160 gtgctttttga tagcc                                                   2175
```

<210> SEQ ID NO 10
<211> LENGTH: 634
<212> TYPE: PRT
<213> ORGANISM: Zea mays

<400> SEQUENCE: 10

```
Leu Ser Leu His Leu Leu Arg Val Ser Pro Ser Pro Phe Ser Phe
 1               5                  10                  15

Arg Ser Pro Leu His Asn Glu Ala Leu Val Ser Arg Asp Met Ala Ser
            20                  25                  30

Gly Leu Glu Glu Lys Leu Ala Gly Leu Ser Thr Gly Gly Asp Gly Gln
        35                  40                  45

Asn Pro Pro Ala Gly Glu Gly Gly Glu Glu Pro Gln Leu Ser Lys
    50                  55                  60

Asn Ala Lys Lys Arg Glu Glu Lys Arg Lys Leu Glu Glu Glu Arg
 65                  70                  75                  80

Arg Leu Lys Glu Glu Glu Lys Lys Asn Lys Ala Ala Ala Ser Gly
                85                  90                  95

Lys Pro Gln Lys Ala Ser Ala Ala Asp Asp Asp Met Asp Pro Thr
            100                 105                 110

Gln Tyr Tyr Glu Asn Arg Leu Lys Ala Leu Asp Ser Leu Lys Ala Thr
        115                 120                 125

Gly Val Asn Pro Tyr Pro His Lys Phe Pro Val Gly Ile Ser Val Pro
    130                 135                 140
```

```
Glu Tyr Ile Glu Lys Tyr Arg Thr Leu Ser Glu Gly Glu Lys Leu Thr
145                 150                 155                 160

Asp Val Ala Glu Cys Leu Ala Gly Arg Ile Met Asn Lys Arg Thr Ser
                165                 170                 175

Ser Ser Lys Leu Phe Phe Tyr Asp Leu Tyr Gly Gly Met Lys Val
            180                 185                 190

Gln Val Met Ala Asp Ala Arg Thr Ser Glu Leu Asp Glu Ala Glu Phe
            195                 200                 205

Ser Lys Tyr His Ser Gly Val Lys Arg Gly Asp Ile Gly Ile Cys
            210                 215                 220

Gly Tyr Pro Gly Lys Ser Asn Arg Gly Glu Leu Ser Val Phe Pro Lys
225                 230                 235                 240

Arg Phe Val Val Leu Ser Pro Cys Leu His Met Met Pro Arg Gln Lys
                245                 250                 255

Gly Glu Gly Ser Ala Val Pro Val Pro Trp Thr Pro Gly Met Gly Arg
            260                 265                 270

Asn Ile Glu Asn Tyr Val Leu Arg Asp Gln Glu Thr Arg Tyr Arg Gln
            275                 280                 285

Arg Tyr Leu Asp Leu Met Val Asn His Glu Val Arg His Ile Phe Lys
            290                 295                 300

Thr Arg Ser Lys Ile Val Ser Phe Ile Arg Lys Phe Leu Asp Asp Arg
305                 310                 315                 320

Glu Phe Leu Glu Val Glu Thr Pro Met Met Asn Met Ile Ala Gly Gly
                325                 330                 335

Ala Ala Ala Arg Pro Phe Val Thr His His Asn Glu Leu Asn Met Arg
            340                 345                 350

Leu Phe Met Arg Ile Ala Pro Glu Leu Tyr Leu Lys Glu Leu Val Val
            355                 360                 365

Gly Gly Leu Asp Arg Val Tyr Glu Ile Gly Lys Gln Phe Arg Asn Glu
            370                 375                 380

Gly Ile Asp Leu Thr His Asn Pro Glu Phe Thr Thr Cys Glu Phe Tyr
385                 390                 395                 400

Met Ala Tyr Ala Asp Tyr Asn Asp Leu Met Glu Leu Thr Glu Thr Met
                405                 410                 415

Leu Ser Gly Met Val Lys Asp Leu Thr Gly Gly Tyr Lys Ile Lys Tyr
            420                 425                 430

His Ala Asn Gly Val Thr Asn Pro Pro Ile Glu Ile Asp Phe Thr Pro
            435                 440                 445

Pro Phe Arg Arg Ile Asp Met Ile Lys Asp Leu Glu Ala Met Ala Asn
    450                 455                 460

Leu Ser Ile Pro Lys Asp Leu Ser Ser Asp Glu Ala Asn Arg Tyr Leu
465                 470                 475                 480

Ile Glu Ala Cys Val Lys Tyr Asp Val Lys Cys Pro Pro Gln Thr
                485                 490                 495

Thr Ser Arg Leu Leu Asp Lys Leu Val Gly His Phe Leu Glu Glu Thr
            500                 505                 510

Cys Val Asn Pro Thr Phe Ile Ile Asn His Pro Glu Ile Met Ser Pro
            515                 520                 525

Leu Ala Lys Trp His Arg Ser Arg Pro Gly Leu Thr Glu Arg Phe Glu
            530                 535                 540

Leu Phe Val Asn Lys His Glu Val Cys Asn Ala Tyr Thr Glu Leu Asn
545                 550                 555                 560

Asp Pro Val Val Gln Arg Gln Arg Phe Glu Glu Gln Leu Lys Asp Arg
```

```
                    565                 570                 575
Gln Ser Gly Asp Asp Glu Ala Met Ala Leu Asp Glu Thr Phe Cys Thr
        580                 585                 590

Ala Leu Glu Tyr Gly Leu Ala Pro Thr Gly Gly Trp Gly Leu Gly Ile
        595                 600                 605

Asp Arg Leu Thr Met Leu Leu Thr Asp Ser Gln Asn Ile Lys Glu Val
        610                 615                 620

Leu Leu Phe Pro Ala Met Lys Pro Gln Glu
625                 630
```

<210> SEQ ID NO 11
<211> LENGTH: 604
<212> TYPE: DNA
<213> ORGANISM: Oryza sativa
<220> FEATURE:
<221> NAME/KEY: unsure
<222> LOCATION: (396)
<223> OTHER INFORMATION: n=a,c,g or t
<220> FEATURE:
<221> NAME/KEY: unsure
<222> LOCATION: (408)
<223> OTHER INFORMATION: n=a,c,g or t
<220> FEATURE:
<221> NAME/KEY: unsure
<222> LOCATION: (478)
<223> OTHER INFORMATION: n=a,c,g or t
<220> FEATURE:
<221> NAME/KEY: unsure
<222> LOCATION: (536)
<223> OTHER INFORMATION: n=a,c,g or t
<220> FEATURE:
<221> NAME/KEY: unsure
<222> LOCATION: (570)
<223> OTHER INFORMATION: n=a,c,g or t
<220> FEATURE:
<221> NAME/KEY: unsure
<222> LOCATION: (573)
<223> OTHER INFORMATION: n=a,c,g or t
<220> FEATURE:
<221> NAME/KEY: unsure
<222> LOCATION: (597)..(598)
<223> OTHER INFORMATION: n=a,c,g or t
<220> FEATURE:
<221> NAME/KEY: unsure
<222> LOCATION: (603)
<223> OTHER INFORMATION: n=a,c,g or t

<400> SEQUENCE: 11 tgactttta gaggtggaga ctccaatgat gaacatgatt gcaggtggag cagctgcaag      60 gcctttgtc acacatcata atgagttaaa catgaggctt tatatgcgta ttgctcctga     120
gctctatctg aaggaattgg ttgttggggg gctggatcgt gtttatgaaa ttgggaagca    180
gttcaggaat gaaggaattg acctgacgca caatcctgaa ttcacaacat gtgaatttta    240
tatggcatat gcagattaca atgacttgat agagcttact gaaaccatgt tatctggtat    300
ggttaaggag ttgacaggtg gctacaagat taaatatcat gctaacggag ttgagaaacc    360
accaatagag attgatttca cacctccctt cagaangata gacatgantg aagaattaga    420
ggctatggct aaactcaata tacctaaaga tctctcaagt gatgaagcaa acaagtantt    480
gatagatgcc tgtgccaaat atgatgtcaa atgcccacct ccccagacta caacanggtt    540
gcttgataag ctagtggcca tttcttggan ggnacatgtg tgaatcccac gtttatnnca    600 acna                                                                 604

<210> SEQ ID NO 12
<211> LENGTH: 125

```
<212> TYPE: PRT
<213> ORGANISM: Oryza sativa

<400> SEQUENCE: 12

Asp Phe Leu Glu Val Glu Thr Pro Met Met Asn Met Ile Ala Gly Gly
 1               5                  10                  15

Ala Ala Ala Arg Pro Phe Val Thr His His Asn Glu Leu Asn Met Arg
            20                  25                  30

Leu Tyr Met Arg Ile Ala Pro Glu Leu Tyr Leu Lys Glu Leu Val Val
        35                  40                  45

Gly Gly Leu Asp Arg Val Tyr Glu Ile Gly Lys Gln Phe Arg Asn Glu
    50                  55                  60

Gly Ile Asp Leu Thr His Asn Pro Glu Phe Thr Thr Cys Glu Phe Tyr
65                  70                  75                  80

Met Ala Tyr Ala Asp Tyr Asn Asp Leu Ile Glu Leu Thr Glu Thr Met
                85                  90                  95

Leu Ser Gly Met Val Lys Glu Leu Thr Gly Gly Tyr Lys Ile Lys Tyr
            100                 105                 110

His Ala Asn Gly Val Glu Lys Pro Leu Asp Lys Leu Val
        115                 120                 125

<210> SEQ ID NO 13
<211> LENGTH: 2143
<212> TYPE: DNA
<213> ORGANISM: Glycine max

<400> SEQUENCE: 13
gcacgagctg agtcagttaa accctagttg ttgtcctcac actctcccaa gcaatggaag      60
ttccttcgga agcgccgtct accggcatcg ccgccgaaac cataagcaaa atgcgctga     120 agcgcgaact caagaacaaa cagaaagaag aagaaaggaa acgcaaggag gaggacaagg     180
ccaaaaaggc agctgaaatg cagaaggcta aggataacaa atctgcacct gctgatgaag     240
atgatatgga cccaactcaa taccttgaga ataggctaaa gtatcttgca gttcaaaagg     300
cagaggggaa taccccctat cctcacaaat tctttgtcac tatgtctctt gatcaataca     360
tcaaggaata tggaggttta agcaacgggc agcacctcga ggatgtctct gtgtctatgg     420
ctggccgaat catgcacaag cgcacctctg gttctaaact cgtctttttat gacctgcaca     480 gtggtggctt caaggtccag gttatggctg atgcgagtaa atcagacttg gatgaggctg     540
aattttccaa attccattct aatgtgaagc gtggggacat agttggtatc actgggtttc     600
caggcaaaag taagaagggt gaacttagta ttttccccaa gacttttgtg ttgctgtctc     660
attgtttgca tatgatgcca aggcaaaagt ctgctgctgc tgcggataat gcaaatttga     720
agaaaaatcc atgggtacca ggaagtacca ggaatcctga acatatatt ttgaaagatc     780 aggaaactag gtatcggtaa cgccatttgg atttgatgct taacccagag ttcgagaaa     840 tatttaagac ccggtctaaa atcatttgtt acattaggag gttccttgat gaccttgatt     900
tcttggaggt tgaaacacca atgatgaaca tgattgctgg tggagctgca gcccgtccat     960
ttgtaactca tcacaatgat cttaacatga ggttattcat gaggattgct ccagaactgt    1020
atcttaagga gttggttgtt ggtggactgg atcgtgttta tgaaattggt aaacaattta    1080
ggaatgaggg catagatttg acccataatc ctgagtttac tacctgtgag ttctatatgg    1140
cttataagga ctacaacgac ttgatggata taacagagca aatgttgagt ggtatggtta    1200
aggaacttac caaagcagct ataaaatcaa gtatcatgct gatgggattg acaaggaacc    1260
```

```
tattgaaatt gactttactc ctccttttag aaggattgac atgattgatg aattagagaa   1320
ggtggcaggc ctaagtattc ccaaagactt gtcgagtgag gaagctaatc aatatttgaa   1380
ggacacatgc ttgaagtatg agatcaaatg tcctcccct gagacaactg ctcgtttgtt    1440
ggataaactt gttggtcact ttttggaaga gacgtgtgta atcctacat tcatcataaa    1500 ccacccctgag atcatgagtc ctttagcaaa gtggcacaga tcaaaacgag gcctgactga  1560
acgttttgaa ttgtttgtta ataagcatga actttgcaat gcatatactg aattgaatga   1620
ccctgtagta caacgacaaa gatttgcaga acaactcaag gatcgacaat caggtgatga   1680
tgaagcaatg gccttcgatg aaacattttg tacggctcta gagtatggtt tgccacctac   1740
tggtggttgg ggtttgggaa ttgatcgttt gaccatgtta ctgacagact cacagaatat   1800
taaggaggtt cttctcttcc ctgccatgaa acctcaagac tgagccttca gtcaaagcta   1860
tgtttaaatc tcagcagtaa aatcatacac ttcaacagga acatgagaaa ggcaagatga   1920
ttaacatggg atctcaattt tgatttatgt acttgattag gagacttgcc atcgactggt   1980
catgcattat ccacatttgt tgatctattt cttaagggcg gttgggaggg acgttattct   2040 agatttttt tgttgttgtg atcgcattga atgtgatgtc ataccagc ttttttttat      2100 tacatacttt gagatttgag acaaaaaaaa aaaaaaaaa aaa                     2143
```

```
<210> SEQ ID NO 14
<211> LENGTH: 599
<212> TYPE: PRT
<213> ORGANISM: Glycine max
<220> FEATURE:
<221> NAME/KEY: UNSURE
<222> LOCATION: (392)..(393)..(394)
<223> OTHER INFORMATION: Xaa = ANY AMINO ACID

<400> SEQUENCE: 14

Leu Thr Leu Ser Gln Ala Met Glu Val Pro Ser Glu Ala Pro Ser Thr
 1               5                  10                  15

Gly Ile Ala Ala Glu Thr Ile Ser Lys Asn Ala Leu Lys Arg Glu Leu
            20                  25                  30

Lys Asn Lys Gln Lys Glu Glu Arg Lys Arg Lys Glu Glu Asp Lys
        35                  40                  45

Ala Lys Lys Ala Ala Glu Met Gln Lys Ala Lys Asp Asn Lys Ser Ala
    50                  55                  60

Pro Ala Asp Glu Asp Asp Met Asp Pro Thr Gln Tyr Leu Glu Asn Arg
65                  70                  75                  80

Leu Lys Tyr Leu Ala Val Gln Lys Ala Glu Gly Asn Asn Pro Tyr Pro
                85                  90                  95

His Lys Phe Phe Val Thr Met Ser Leu Asp Gln Tyr Ile Lys Glu Tyr
            100                 105                 110

Gly Gly Leu Ser Asn Gly Gln His Leu Glu Asp Val Ser Val Ser Met
        115                 120                 125

Ala Gly Arg Ile Met His Lys Arg Thr Ser Gly Ser Lys Leu Val Phe
    130                 135                 140

Tyr Asp Leu His Ser Gly Gly Phe Lys Val Gln Val Met Ala Asp Ala
145                 150                 155                 160

Ser Lys Ser Asp Leu Asp Glu Ala Glu Phe Ser Lys Phe His Ser Asn
                165                 170                 175

Val Lys Arg Gly Asp Ile Val Gly Ile Thr Gly Phe Pro Gly Lys Ser
            180                 185                 190

Lys Lys Gly Glu Leu Ser Ile Phe Pro Lys Thr Phe Val Leu Leu Ser
```

-continued

```
                195                 200                 205
His Cys Leu His Met Met Pro Arg Gln Lys Ser Ala Ala Ala Asp
    210                 215                 220
Asn Ala Asn Leu Lys Lys Asn Pro Trp Val Pro Gly Ser Thr Arg Asn
225                 230                 235                 240
Pro Glu Thr Tyr Ile Leu Lys Asp Gln Glu Thr Arg Tyr Arg Arg His
                245                 250                 255
Leu Asp Leu Met Leu Asn Pro Glu Val Arg Glu Ile Phe Lys Thr Arg
                260                 265                 270
Ser Lys Ile Ile Cys Tyr Ile Arg Arg Phe Leu Asp Asp Leu Asp Phe
            275                 280                 285
Leu Glu Val Glu Thr Pro Met Met Asn Met Ile Ala Gly Gly Ala Ala
            290                 295                 300
Ala Arg Pro Phe Val Thr His His Asn Asp Leu Asn Met Arg Leu Phe
305                 310                 315                 320
Met Arg Ile Ala Pro Glu Leu Tyr Leu Lys Glu Leu Val Val Gly Gly
                325                 330                 335
Leu Asp Arg Val Tyr Glu Ile Gly Lys Gln Phe Arg Asn Glu Gly Ile
            340                 345                 350
Asp Leu Thr His Asn Pro Glu Phe Thr Thr Cys Glu Phe Tyr Met Ala
            355                 360                 365
Tyr Lys Asp Tyr Asn Asp Leu Met Asp Ile Thr Glu Gln Met Leu Ser
        370                 375                 380
Gly Met Val Lys Glu Leu Thr Xaa Xaa Xaa Tyr Lys Ile Lys Tyr His
385                 390                 395                 400
Ala Asp Gly Ile Asp Lys Glu Pro Ile Glu Ile Asp Phe Thr Pro Pro
                405                 410                 415
Phe Arg Arg Ile Asp Met Ile Asp Glu Leu Glu Lys Val Ala Gly Leu
                420                 425                 430
Ser Ile Pro Lys Asp Leu Ser Ser Glu Glu Ala Asn Gln Tyr Leu Lys
            435                 440                 445
Asp Thr Cys Leu Lys Tyr Glu Ile Lys Cys Pro Pro Pro Glu Thr Thr
    450                 455                 460
Ala Arg Leu Leu Asp Lys Leu Val Gly His Phe Leu Glu Glu Thr Cys
465                 470                 475                 480
Val Asn Pro Thr Phe Ile Ile Asn His Pro Glu Ile Met Ser Pro Leu
                485                 490                 495
Ala Lys Trp His Arg Ser Lys Arg Gly Leu Thr Glu Arg Phe Glu Leu
            500                 505                 510
Phe Val Asn Lys His Glu Leu Cys Asn Ala Tyr Thr Glu Leu Asn Asp
            515                 520                 525
Pro Val Val Gln Arg Gln Arg Phe Ala Glu Gln Leu Lys Asp Arg Gln
        530                 535                 540
Ser Gly Asp Asp Glu Ala Met Ala Phe Asp Glu Thr Phe Cys Thr Ala
545                 550                 555                 560
Leu Glu Tyr Gly Leu Pro Pro Thr Gly Gly Trp Gly Leu Gly Ile Asp
                565                 570                 575
Arg Leu Thr Met Leu Leu Thr Asp Ser Gln Asn Ile Lys Glu Val Leu
                580                 585                 590
Leu Phe Pro Ala Met Lys Pro
            595
```

<210> SEQ ID NO 15

<211> LENGTH: 702
<212> TYPE: DNA
<213> ORGANISM: Triticum aestivum

<400> SEQUENCE: 15

```
gcacgaggct tgacaagcta gtgggccatt tcttggagga acatgtgtg aacccaacat      60
ttattatcaa ccacccagag ataatgagtc cattggcaaa gtggcatagg tcccgacctg    120
ggttgacaga aaggtttgag ctctttgtta acaaacacga ggtgtgcaat gcctacactg    180
agttgaacga tcctgttgtg caaaggcaac ggtttgagga acaactaaag gatcgtcaat    240
ctggtgatga tgaagctatg gctttggacg aaacattctg cactgccctc gagtatgggc    300
tgcctccgac aggtggttgg ggtttgggaa ttgatcgcct tacaatgatg ctgacagatt    360
cccagaacat caaggaagtt ctcttgttcc cggccatgaa gccccaagag tagctgtttg    420
caagcccatc aacagagtaa ttttgttttg ctgcgctgag gttggaggat tatgacatgt    480
gacaatacaa cgagttttaa ctgtgccgga caaaacatgt gtagcagcac tggaggtaca    540
agctactttt gcgtggaagg gttgttgaaa atttgaactc cggttaggag aagagtgag     600
gcatatgaag caagaatcag aaggagacag tgtgctacat gtttgcttgt tttcttttg     660
gaagatcaaa atttagtgct tggtattgtt atacactttt tt                       702
```

<210> SEQ ID NO 16
<211> LENGTH: 136
<212> TYPE: PRT
<213> ORGANISM: Triticum aestivum

<400> SEQUENCE: 16

```
Thr Arg Leu Asp Lys Leu Val Gly His Phe Leu Glu Glu Thr Cys Val
 1               5                  10                  15

Asn Pro Thr Phe Ile Ile Asn His Pro Glu Ile Met Ser Pro Leu Ala
            20                  25                  30

Lys Trp His Arg Ser Arg Pro Gly Leu Thr Glu Arg Phe Glu Leu Phe
        35                  40                  45

Val Asn Lys His Glu Val Cys Asn Ala Tyr Thr Glu Leu Asn Asp Pro
    50                  55                  60

Val Val Gln Arg Gln Arg Phe Glu Gln Leu Lys Asp Arg Gln Ser
 65                  70                  75                  80

Gly Asp Asp Glu Ala Met Ala Leu Asp Glu Thr Phe Cys Thr Ala Leu
                85                  90                  95

Glu Tyr Gly Leu Pro Pro Thr Gly Gly Trp Gly Leu Gly Ile Asp Arg
            100                 105                 110

Leu Thr Met Met Leu Thr Asp Ser Gln Asn Ile Lys Glu Val Leu Leu
        115                 120                 125

Phe Pro Ala Met Lys Pro Gln Glu
    130                 135
```

<210> SEQ ID NO 17
<211> LENGTH: 1430
<212> TYPE: DNA
<213> ORGANISM: Zea mays

<400> SEQUENCE: 17

```
cgaaccgctc gctgctggct cctccgcgcg cgtgttcgcg gcatggccac gcttccaatg       60
gcgctctccc ccgccgccat ttccccctcc accaccctcc ccctctacta ttcttcgcgt      120
cctcaccgcc gcctcctcgc ccgcttcttc tccgtcgctt cggcaccggg cggagcgaaa      180
```

-continued

```
gggcaccgac cggcggcctc cgccgttgag gtgggcggcg tcaagatcgc gcgcgaggat    240
gttgtgaagg aggatgatcc gacaaacaac gtgcccgaca atatcttttc gaagatcggc    300
ctgcagctgc acaggaggga taaccatccc cttgggattt tgaagaacac aatttatgat    360
tactttgaca agaacttcac tgggcagttt gacaagtttg atgacctttg ccctcttgtt    420
tctgtcaagc agaattttga tgatgtcttg gtcccttctg accatgtaag ccggagttac    480
aacgacacat attatgttga tggtcaaaca gtcttaaggt gtcataccag tgctcatcaa    540
gctgagctgc taaggcatgg acatacacac tttcttgtaa ctggagatgt ttaccgtagg    600
gattccattg attcaactca ctatcctgtc ttccatcaga tggaagggtt ccgtgtcttc    660
tctcctgatg aatggtcagg gtctcgcatg ggtgggacag catatgcagc tgcagaactc    720
aagaaaacac tggaaggctt ggcaagacat ctatttggtg ctgtagagat gcgatgggtt    780
gacacttact cccatttac caacccatcc tttgagctcg aaatatactt tcaggatgat    840
tggttggagg ttttggggtg tggagtcacc gagcaggaaa ttttgaaaag aaatggcagg    900
agggaccatg tggcatgggc ctttggattg gcttggagc gccttgcaat ggtccttttc    960
gacattccag atattcgact attctggtcg aatgataaac ggttcacgtc ccagttctca   1020
gaaggcaagc ttggtgtcaa gttcaagcca ttttcaaagt ttcctccttg ttacaaggat   1080
atgagtttct ggatcaatga tgcatttaca gaaaacaact tatgtgaggt tgtcagagga   1140
attgctggtg atcttgttga ggaggtaaaa cttattgata atttcacgaa caagaaaggc   1200
atgacgagcc attgctatag aatagcctat aggtcgatgg aacgctcgct cacagacgag   1260
gagattaaca atcttcagtt gaatgtcagg gaagctgtga agataaatt ggaagtagag   1320 ttgagataga agcagctagc tatgcagtta taccatgaac taaattttgc ctctctttat   1380
atgtaaatcc atttaaaatg attttttttgt atctatcaag aaaatgcacc               1430
```

<210> SEQ ID NO 18
<211> LENGTH: 442
<212> TYPE: PRT
<213> ORGANISM: Zea mays

<400> SEQUENCE: 18

```
Arg Thr Ala Arg Cys Trp Leu Leu Arg Ala Arg Val Arg Gly Met Ala
  1               5                  10                  15

Thr Leu Pro Met Ala Leu Ser Pro Ala Ala Ile Ser Pro Phe Thr Thr
                 20                  25                  30

Leu Pro Leu Tyr Tyr Ser Ser Arg Pro His Arg Leu Leu Ala Arg
         35                  40                  45

Phe Phe Ser Val Ala Ser Ala Pro Gly Gly Ala Lys Gly His Arg Pro
     50                  55                  60

Ala Ala Ser Ala Val Glu Val Gly Val Lys Ile Ala Arg Glu Asp
 65                  70                  75                  80

Val Val Lys Glu Asp Asp Pro Thr Asn Asn Val Pro Asp Asn Ile Phe
                 85                  90                  95

Ser Lys Ile Gly Leu Gln Leu His Arg Arg Asp Asn His Pro Leu Gly
            100                 105                 110

Ile Leu Lys Asn Thr Ile Tyr Asp Tyr Phe Asp Lys Asn Phe Thr Gly
        115                 120                 125

Gln Phe Asp Lys Phe Asp Asp Leu Cys Pro Leu Val Ser Val Lys Gln
    130                 135                 140

Asn Phe Asp Asp Val Leu Val Pro Ser Asp His Val Ser Arg Ser Tyr
145                 150                 155                 160
```

```
Asn Asp Thr Tyr Tyr Val Asp Gly Gln Thr Val Leu Arg Cys His Thr
            165                 170                 175
Ser Ala His Gln Ala Glu Leu Leu Arg His Gly His Thr His Phe Leu
            180                 185                 190
Val Thr Gly Asp Val Tyr Arg Asp Ser Ile Asp Ser Thr His Tyr
            195                 200                 205
Pro Val Phe His Gln Met Glu Gly Phe Arg Val Phe Ser Pro Asp Glu
    210                 215                 220
Trp Ser Gly Ser Arg Met Gly Gly Thr Ala Tyr Ala Ala Glu Leu
225                 230                 235                 240
Lys Lys Thr Leu Glu Gly Leu Ala Arg His Leu Phe Gly Ala Val Glu
            245                 250                 255
Met Arg Trp Val Asp Thr Tyr Phe Pro Phe Thr Asn Pro Ser Phe Glu
            260                 265                 270
Leu Glu Ile Tyr Phe Gln Asp Asp Trp Leu Glu Val Leu Gly Cys Gly
            275                 280                 285
Val Thr Glu Gln Glu Ile Leu Lys Arg Asn Gly Arg Arg Asp His Val
            290                 295                 300
Ala Trp Ala Phe Gly Leu Gly Leu Glu Arg Leu Ala Met Val Leu Phe
305                 310                 315                 320
Asp Ile Pro Asp Ile Arg Leu Phe Trp Ser Asn Asp Lys Arg Phe Thr
            325                 330                 335
Ser Gln Phe Ser Glu Gly Lys Leu Gly Val Lys Phe Lys Pro Phe Ser
            340                 345                 350
Lys Phe Pro Pro Cys Tyr Lys Asp Met Ser Phe Trp Ile Asn Asp Ala
            355                 360                 365
Phe Thr Glu Asn Asn Leu Cys Glu Val Val Arg Gly Ile Ala Gly Asp
            370                 375                 380
Leu Val Glu Glu Val Lys Leu Ile Asp Asn Phe Thr Asn Lys Lys Gly
385                 390                 395                 400
Met Thr Ser His Cys Tyr Arg Ile Ala Tyr Arg Ser Met Glu Arg Ser
            405                 410                 415
Leu Thr Asp Glu Glu Ile Asn Asn Leu Gln Leu Asn Val Arg Glu Ala
            420                 425                 430
Val Lys Asp Lys Leu Glu Val Glu Leu Arg
            435                 440

<210> SEQ ID NO 19
<211> LENGTH: 1000
<212> TYPE: DNA
<213> ORGANISM: Oryza sativa

<400> SEQUENCE: 19
gcacgagtgg taccaacagc atcctgctcg ggattcacac gatacatttt ttcttgaagc      60
ccctgccgct acaaaacaat tgcctgaaga ttatcttgag aaagtaaagg aagttcatca     120
acgtggtggt tatggctcca agggatatgg ctatgactgg aaacgggatg aagcagagaa     180
aaacctgctt cgtacccaca ctacagcagt ttcaacaagg atgctataca agctagcaca     240
agagaaacct tttgccccta gaggtactac tccattgat cgtgttttcc gcaatgaagc     300
tgtggaccgg actcatcttg cggaattcca ccagattgaa ggtctcattt gtgattatgg     360
tttgacgctg ggtgatctga ttggtgtatt ggaggatttc ttctcgagtc taggcatgtc     420
aaagctgcgt ttcaagcctg cctacaatcc atacaccgag ccgagcatgg aaattttcag     480
```

-continued

```
ttaccatgaa ggtttgaaga aatgggtgga agttggtaac tctggcatgt tcagacctga    540
aatgttactt cccatgggac tgccagaggg tgttaatgtt attgcatggg gtctttcact    600
agaaaggcca acaatgattc tttacggcat cgacaacatt cgagacctct ttggaccaaa    660
ggttgatttc aacctcatca agagcaaccc tctctgccgc ttgggactgc agtaaaacct    720
tgcaaaagtt ggttggaagt gattaagtaa caagatttgt ttagttgatc agtggttgaa    780
cgtgaagaga tcatttctgg cttaccttga aacaccaata catgtgcatt tagcagaggt    840
ttttgtatta cagttttgag tgatatgaga ctaccagcca attttgtgt gtgtccatat     900 tcgaatactt tgatacattt taattgagca catccaatgt atgaagtggt catctgccgc    960
tgcggttgct tgaatcaaaa aaaaaaaaaa aaaaaaaaa                          1000
```

<210> SEQ ID NO 20
<211> LENGTH: 237
<212> TYPE: PRT
<213> ORGANISM: Oryza sativa

<400> SEQUENCE: 20

```
His Glu Trp Tyr Gln Gln His Pro Ala Arg Asp Ser His Asp Thr Phe
  1               5                  10                  15

Phe Leu Glu Ala Pro Ala Ala Thr Lys Gln Leu Pro Glu Asp Tyr Leu
             20                  25                  30

Glu Lys Val Lys Glu Val His Gln Arg Gly Gly Tyr Gly Ser Lys Gly
         35                  40                  45

Tyr Gly Tyr Asp Trp Lys Arg Asp Glu Ala Glu Lys Asn Leu Leu Arg
     50                  55                  60

Thr His Thr Thr Ala Val Ser Thr Arg Met Leu Tyr Lys Leu Ala Gln
 65                  70                  75                  80

Glu Lys Pro Phe Ala Pro Lys Arg Tyr Tyr Ser Ile Asp Arg Val Phe
                 85                  90                  95

Arg Asn Glu Ala Val Asp Arg Thr His Leu Ala Glu Phe His Gln Ile
            100                 105                 110

Glu Gly Leu Ile Cys Asp Tyr Gly Leu Thr Leu Gly Asp Leu Ile Gly
        115                 120                 125

Val Leu Glu Asp Phe Phe Ser Ser Leu Gly Met Ser Lys Leu Arg Phe
    130                 135                 140

Lys Pro Ala Tyr Asn Pro Tyr Thr Glu Pro Ser Met Glu Ile Phe Ser
145                 150                 155                 160

Tyr His Glu Gly Leu Lys Lys Trp Val Glu Val Gly Asn Ser Gly Met
                165                 170                 175

Phe Arg Pro Glu Met Leu Leu Pro Met Gly Leu Pro Glu Gly Val Asn
            180                 185                 190

Val Ile Ala Trp Gly Leu Ser Leu Glu Arg Pro Thr Met Ile Leu Tyr
        195                 200                 205

Gly Ile Asp Asn Ile Arg Asp Leu Phe Gly Pro Lys Val Asp Phe Asn
    210                 215                 220

Leu Ile Lys Ser Asn Pro Leu Cys Arg Leu Gly Leu Gln
225                 230                 235
```

<210> SEQ ID NO 21
<211> LENGTH: 387
<212> TYPE: DNA
<213> ORGANISM: Glycine max
<220> FEATURE:
<221> NAME/KEY: unsure
<222> LOCATION: (337)

```
<223> OTHER INFORMATION: n=a,c,g or t
<220> FEATURE:
<221> NAME/KEY: unsure
<222> LOCATION: (379)
<223> OTHER INFORMATION: n=a,c,g or t

<400> SEQUENCE: 21
gattgccaat ggatcatgga agaaaaatc attcaaatct ttgaatttag gaaaaggagt      60
catgggtgtc cctccaaatg gtggccatct tcacacttta cttaaatgca gaactatgat    120
gaaagaaatc ttcttggaaa tgggatttga agaaatgcca accaacaatt acgttgaatc    180
ttctttctgg aattttgata ctttatttca acctcaacaa catcctgctc gtgatgctca    240
cgatactttc ttccttttctg aacctgcatc tgccaaatcc attccacaag attatttaga   300
aagagtgaaa acaatgcatg agaaggagg gcacggntct attggttgga gatacgactg     360
gagtggaaac tgagtccana aaaaaaa                                         387

<210> SEQ ID NO 22
<211> LENGTH: 123
<212> TYPE: PRT
<213> ORGANISM: Glycine max

<400> SEQUENCE: 22

Ile Ala Asn Gly Ser Trp Lys Glu Lys Ser Phe Lys Ser Leu Asn Leu
  1               5                  10                  15

Gly Lys Gly Val Met Gly Val Pro Pro Asn Gly Gly His Leu His Thr
             20                  25                  30

Leu Leu Lys Cys Arg Thr Met Met Lys Glu Ile Phe Leu Glu Met Gly
         35                  40                  45

Phe Glu Glu Met Pro Thr Asn Asn Tyr Val Glu Ser Ser Phe Trp Asn
     50                  55                  60

Phe Asp Thr Leu Phe Gln Pro Gln Gln His Pro Ala Arg Asp Ala His
 65                  70                  75                  80

Asp Thr Phe Phe Leu Ser Glu Pro Ala Ser Ala Lys Ser Ile Pro Gln
                 85                  90                  95

Asp Tyr Leu Glu Arg Val Lys Thr Met His Glu Lys Gly Gly His Gly
            100                 105                 110

Ser Ile Gly Trp Arg Tyr Asp Trp Ser Gly Asn
        115                 120

<210> SEQ ID NO 23
<211> LENGTH: 1074
<212> TYPE: DNA
<213> ORGANISM: Triticum aestivum

<400> SEQUENCE: 23
gcacgaggga caacctattg cgataggata tagccaaccg ttgttagagg tccgtgaggc      60
aatccagaac attttctcg agatgggtt cagtgagatg ccaacgaaca tgtatgtaga      120
gagcagcttc tggaattttg atgcactgtt ccagccacaa cagcatcctg ctcgtgattc    180
acacgatacc ttttcctca aagcccctgc tacaacaaca caattacctg atgactatct     240
tgagaaagta aagcaagtac atcagtctgg tggtcatggc tccaaaggat atggttacga    300
ttggaagcga gatgaagcag agaaaaacct gcttcgtact cacacaactg cagtttcaac    360
aaggatgcta tacaagctag cacaggagaa aactttgct cctaagagat actattctat     420
tgatcgtgtt ttccggaatg aagctgtgga ccgaactcat cttgcagaat ccaccagat     480 agaaggtctt atttgtgatt atggtttgac gcttggtgat ctgataggtg tattggagga    540
```

```
tttcttctcc agactaggca tgtcaaagct gcgtttcaaa cctgcctaca acccgtacac    600
tgaaccaagc atggaaattt tcagctacca cgatggtctg aagaaatggg tggaaatagg    660
caactcaggc atgttcaggc cggaaatgtt acttcccatg ggactgccag agggtgttaa    720
tgttatcgca tggggtcttt cgcttgaaag gccaacaatg attctgtatg ggattgacaa    780
catacgtgat ctctttgggc caaggtcga cttcaatctg atcaagagca gcccgatttg    840
ccgcttgggg ctgtagtgtg gtgagcttga tagaacttta tctggatgtc tggatgcgaa    900
ggatgtttat ttgtggttat acctttgaaa accagtactt gtgcatttaa cagagggagt    960
gcagaaatac acacatgtag ctctgaattg caaaaaaaaa aaaaaaaaaa aaaaaaaaa    1020 aataaaaaaa aaacaaaaaa aaaaaaaaaa tactcgaggg ggggccgtac caca          1074
```

<210> SEQ ID NO 24
<211> LENGTH: 284
<212> TYPE: PRT
<213> ORGANISM: Triticum aestivum

<400> SEQUENCE: 24

```
His Glu Gly Gln Pro Ile Ala Ile Gly Tyr Ser Gln Pro Leu Leu Glu
  1               5                  10                  15

Val Arg Glu Ala Ile Gln Asn Ile Phe Leu Glu Met Gly Phe Ser Glu
                 20                  25                  30

Met Pro Thr Asn Met Tyr Val Glu Ser Ser Phe Trp Asn Phe Asp Ala
             35                  40                  45

Leu Phe Gln Pro Gln Gln His Pro Ala Arg Asp Ser His Asp Thr Phe
         50                  55                  60

Phe Leu Lys Ala Pro Ala Thr Thr Gln Leu Pro Asp Asp Tyr Leu
 65                  70                  75                  80

Glu Lys Val Lys Gln Val His Gln Ser Gly Gly His Gly Ser Lys Gly
                 85                  90                  95

Tyr Gly Tyr Asp Trp Lys Arg Asp Glu Ala Glu Lys Asn Leu Leu Arg
            100                 105                 110

Thr His Thr Thr Ala Val Ser Thr Arg Met Leu Tyr Lys Leu Ala Gln
        115                 120                 125

Glu Lys Thr Phe Ala Pro Lys Arg Tyr Tyr Ser Ile Asp Arg Val Phe
    130                 135                 140

Arg Asn Glu Ala Val Asp Arg Thr His Leu Ala Glu Phe His Gln Ile
145                 150                 155                 160

Glu Gly Leu Ile Cys Asp Tyr Gly Leu Thr Leu Gly Asp Leu Ile Gly
                165                 170                 175

Val Leu Glu Asp Phe Phe Ser Arg Leu Gly Met Ser Lys Leu Arg Phe
            180                 185                 190

Lys Pro Ala Tyr Asn Pro Tyr Thr Glu Pro Ser Met Glu Ile Phe Ser
        195                 200                 205

Tyr His Asp Gly Leu Lys Lys Trp Val Glu Ile Gly Asn Ser Gly Met
    210                 215                 220

Phe Arg Pro Glu Met Leu Leu Pro Met Gly Leu Pro Glu Gly Val Asn
225                 230                 235                 240

Val Ile Ala Trp Gly Leu Ser Leu Glu Arg Pro Thr Met Ile Leu Tyr
                245                 250                 255

Gly Ile Asp Asn Ile Arg Asp Leu Phe Gly Pro Lys Val Asp Phe Asn
            260                 265                 270

Leu Ile Lys Ser Ser Pro Ile Cys Arg Leu Gly Leu
        275                 280
```

<210> SEQ ID NO 25
<211> LENGTH: 1939
<212> TYPE: DNA
<213> ORGANISM: Zea mays

<400> SEQUENCE: 25

| | | | | | | |
|---|---|---|---|---|---|---|
| gtccggaatt | cccgggtcga | cccacgcgtc | cgtgctgtcc | cattggcaac | ttgcgcgcta | 60 |
| ctctgactcg | agtggccgct | actctacccc | acccacaccc | ttccgcccgc | cgccactaaa | 120 |
| ccctagcggg | acaccgcct | tgctcgcgcc | gcctcatcct | ctcactcctc | tcggaccccc | 180 |
| ggtggccggt | gcagagctgc | gcgaccgaga | accgaatctg | tgagccatgt | cgaccaacaa | 240 |
| gggcagcgcg | gccaagggcg | gcggagggaa | gaagaaggag | gtgaagaagg | agacgaagct | 300 |
| cgggatggcc | tataagaagg | acgacaactt | cggggagtgg | tactccgagg | ttgttgttaa | 360 |
| cagtgaaatg | attgagtact | atgacatttc | tggttgttat | atattgaggc | catgggcgat | 420 |
| ggaaatctgg | gagctactga | agaattctt | tgatgcagaa | attaaaaagc | tgaagctcaa | 480 |
| accatattat | ttccctttgt | ttgttactga | gaatgttcta | cagaaggaaa | aggaccacat | 540 |
| tgagggcttt | gcacctgagg | tagcttgggt | tactaaatct | gggaaatctg | acctggaagc | 600 |
| accgattgca | atccgcccca | caagtgagac | tgtcatgtat | ccgtacttct | ccaaatggat | 660 |
| aagaagccac | cgagacttac | ccttgaggtg | taatcaatgg | tgtaatgttg | ttagatggga | 720 |
| gtttagcaat | ccaactcctt | tcataaggag | ccgtgaattt | ctgtggcaag | aggggcatac | 780 |
| tgcttttgcg | actaagaag | aggcagatga | agaggttctc | caaatattgg | aactgtaccg | 840 |
| aaggatatac | gaagaatttt | tagcagttcc | agtttccaaa | gggagaaaaa | gcgagatgga | 900 |
| aaaatttgca | ggtggccttt | ataccaccag | cgttgaggcc | ttcattccaa | acactggtcg | 960 |
| tggcatacaa | ggcgcaacct | cacactgtct | tggtcaaaac | tttgccaaga | tgtttgatat | 1020 |
| cacttttgag | aatgagaaag | gtgttaggga | atggtttgg | caaaactctt | gggcctacac | 1080 |
| aacccgctcg | attggagtga | tggtgatgac | acatggtgat | gacaaaggct | tagtattacc | 1140 |
| accaaaggtg | gcaccaatcc | aggtaatcgt | gatttcagtg | ccttataagg | acgctgacac | 1200 |
| aactgccata | aagggagcct | gcgaatcaac | tgtttacaca | ctcgatcaat | ctgggattag | 1260 |
| agcggatcag | gacacccgtg | aaaattactc | tccaggttgg | aagtattccc | actgggaaat | 1320 |
| gaaaggtgtt | ccattgagaa | ttgagattgg | tccaaaagat | ctggcaaaca | aacaggtgcg | 1380 |
| tgttgtccgc | cgggacaacg | gtgcaaaggt | tgacatccct | gtgaccaatt | tggttgaaga | 1440 |
| ggttaaagtg | ttactggatg | agattcaaaa | aaatctgttc | aaaacagccc | aagaaaagag | 1500 |
| agatgcctgt | gttcatgtcg | tgaacacttg | ggatgaattc | acaactgctc | tgaataacaa | 1560 |
| aaagttgatc | ttggctccat | ggtgtgatga | ggaggaaatt | gagaaagatg | taaaaactcg | 1620 |
| gacaaaaggg | gaacttggag | ctgcgaaaac | attgtgtact | ccatttgagc | agccagaact | 1680 |
| tccagaaggt | accctgtgct | ttgcatctgg | aaagccagcg | aagaagtggt | cgttctgggg | 1740 |
| ccgcagctac | tgattgcctg | tgctgggatt | atttctggat | tcagttctag | tgagttatgt | 1800 |
| agctttgaag | tgtcggatac | aaatccaaaa | atccatttac | attgcgttt | acatcgactt | 1860 |
| gcagttctca | tgtcatcact | gctgacaaaa | gccatcgatt | tcctgtggac | catgctattc | 1920 |
| gagtttgaat | gttgcaagg | | | | | 1939 |

<210> SEQ ID NO 26
<211> LENGTH: 383

```
<212> TYPE: PRT
<213> ORGANISM: Zea mays

<400> SEQUENCE: 26

Pro Ile Ala Ile Arg Pro Thr Ser Glu Thr Val Met Tyr Pro Tyr Phe
  1               5                  10                  15

Ser Lys Trp Ile Arg Ser His Arg Asp Leu Pro Leu Arg Cys Asn Gln
             20                  25                  30

Trp Cys Asn Val Val Arg Trp Glu Phe Ser Asn Pro Thr Pro Phe Ile
         35                  40                  45

Arg Ser Arg Glu Phe Leu Trp Gln Glu Gly His Thr Ala Phe Ala Thr
     50                  55                  60

Lys Glu Glu Ala Asp Glu Val Leu Gln Ile Leu Glu Leu Tyr Arg
 65                  70                  75                  80

Arg Ile Tyr Glu Glu Phe Leu Ala Val Pro Val Ser Lys Gly Arg Lys
                 85                  90                  95

Ser Glu Met Glu Lys Phe Ala Gly Gly Leu Tyr Thr Thr Ser Val Glu
            100                 105                 110

Ala Phe Ile Pro Asn Thr Gly Arg Gly Ile Gln Gly Ala Thr Ser His
        115                 120                 125

Cys Leu Gly Gln Asn Phe Ala Lys Met Phe Asp Ile Thr Phe Glu Asn
130                 135                 140

Glu Lys Gly Val Arg Glu Met Val Trp Gln Asn Ser Trp Ala Tyr Thr
145                 150                 155                 160

Thr Arg Ser Ile Gly Val Met Val Met Thr His Gly Asp Asp Lys Gly
                165                 170                 175

Leu Val Leu Pro Pro Lys Val Ala Pro Ile Gln Val Ile Val Ile Ser
            180                 185                 190

Val Pro Tyr Lys Asp Ala Asp Thr Thr Ala Ile Lys Gly Ala Cys Glu
        195                 200                 205

Ser Thr Val Tyr Thr Leu Asp Gln Ser Gly Ile Arg Ala Asp Gln Asp
210                 215                 220

Thr Arg Glu Asn Tyr Ser Pro Gly Trp Lys Tyr Ser His Trp Glu Met
225                 230                 235                 240

Lys Gly Val Pro Leu Arg Ile Glu Ile Gly Pro Lys Asp Leu Ala Asn
                245                 250                 255

Lys Gln Val Arg Val Arg Arg Asp Asn Gly Ala Lys Val Asp Ile
            260                 265                 270

Pro Val Thr Asn Leu Val Glu Glu Val Lys Val Leu Leu Asp Glu Ile
        275                 280                 285

Gln Lys Asn Leu Phe Lys Thr Ala Gln Glu Lys Arg Asp Ala Cys Val
290                 295                 300

His Val Val Asn Thr Trp Asp Glu Phe Thr Thr Ala Leu Asn Asn Lys
305                 310                 315                 320

Lys Leu Ile Leu Ala Pro Trp Cys Asp Glu Glu Ile Glu Lys Asp
                325                 330                 335

Val Lys Thr Arg Thr Lys Gly Glu Leu Gly Ala Ala Lys Thr Leu Cys
            340                 345                 350

Thr Pro Phe Glu Gln Pro Glu Leu Pro Glu Gly Thr Leu Cys Phe Ala
        355                 360                 365

Ser Gly Lys Pro Ala Lys Lys Trp Ser Phe Trp Gly Arg Ser Tyr
370                 375                 380

<210> SEQ ID NO 27
```

```
<211> LENGTH: 697
<212> TYPE: DNA
<213> ORGANISM: Glycine max
<220> FEATURE:
<221> NAME/KEY: unsure
<222> LOCATION: (11)
<223> OTHER INFORMATION: n=a,c,g or t
<220> FEATURE:
<221> NAME/KEY: unsure
<222> LOCATION: (40)
<223> OTHER INFORMATION: n=a,c,g or t
<220> FEATURE:
<221> NAME/KEY: unsure
<222> LOCATION: (42)
<223> OTHER INFORMATION: n=a,c,g or t
<220> FEATURE:
<221> NAME/KEY: unsure
<222> LOCATION: (91)
<223> OTHER INFORMATION: n=a,c,g or t
<220> FEATURE:
<221> NAME/KEY: unsure
<222> LOCATION: (118)
<223> OTHER INFORMATION: n=a,c,g or t
<220> FEATURE:
<221> NAME/KEY: unsure
<222> LOCATION: (183)
<223> OTHER INFORMATION: n=a,c,g or t
<220> FEATURE:
<221> NAME/KEY: unsure
<222> LOCATION: (266)
<223> OTHER INFORMATION: n=a,c,g or t
<220> FEATURE:
<221> NAME/KEY: unsure
<222> LOCATION: (304)
<223> OTHER INFORMATION: n=a,c,g or t
<220> FEATURE:
<221> NAME/KEY: unsure
<222> LOCATION: (503)
<223> OTHER INFORMATION: n=a,c,g or t
<220> FEATURE:
<221> NAME/KEY: unsure
<222> LOCATION: (632)
<223> OTHER INFORMATION: n=a,c,g or t
<220> FEATURE:
<221> NAME/KEY: unsure
<222> LOCATION: (694)
<223> OTHER INFORMATION: n=a,c,g or t

<400> SEQUENCE: 27
gtgaaacagt natgtatccc tactactcta agtggataan ngacatcgt gacttgcctt       60 tgaaacttaa tcagtggtgc aatgttgtaa natgggagtt cagcaacccc actccatnca     120
tcaggagtcg cgagtttctt tggcaagaag ggcacactgc ttttgcaaca aaggatgaag     180
canatgcaga agttcttgag attctggaat tatataggcg tatatacgaa gagtatttgg     240
cagttcctgt cataaagggt aagaanagtg agcttgagaa gtttgctggt ggactctaca     300
ctancaatgt tgaggcattt attccaaaca ctggtcgtgg tatccaaggt gcaacttctc     360
attgtttggg ccaaaatttt gctaaaatgt ttgagataaa ctttgaaaat gaaaagggag     420
agaaagcaat ggtctggcag aattcatggg cctatagtac tcgaactatt ggggtcatgg     480
tgatggttca tggtgatgac aangggattg gtactacctc ctaaagtagc atcagtacaa     540
gttattgtga ttcctgtgcc ttacaaagat gccgatactc aaggaatctt tgatgcctgt     600
ctgcactgtg aatacattga tgaagcagga tngcgctgag cagatctaga gatatatctc     660
ctggatgaga tccactggga atgaaagggt ctcnaga                              697

<210> SEQ ID NO 28
<211> LENGTH: 173
<212> TYPE: PRT
<213> ORGANISM: Glycine max
```

```
<220> FEATURE:
<221> NAME/KEY: UNSURE
<222> LOCATION: (13)..(14)
<223> OTHER INFORMATION: Xaa = ANY AMINO ACID
<220> FEATURE:
<221> NAME/KEY: UNSURE
<222> LOCATION: (30)
<223> OTHER INFORMATION: Xaa = ANY AMINO ACID
<220> FEATURE:
<221> NAME/KEY: UNSURE
<222> LOCATION: (39)
<223> OTHER INFORMATION: Xaa = ANY AMINO ACID
<220> FEATURE:
<221> NAME/KEY: UNSURE
<222> LOCATION: (61)
<223> OTHER INFORMATION: Xaa = ANY AMINO ACID
<220> FEATURE:
<221> NAME/KEY: UNSURE
<222> LOCATION: (88)
<223> OTHER INFORMATION: Xaa = ANY AMINO ACID
<220> FEATURE:
<221> NAME/KEY: UNSURE
<222> LOCATION: (101)
<223> OTHER INFORMATION: Xaa = ANY AMINO ACID
<220> FEATURE:
<221> NAME/KEY: UNSURE
<222> LOCATION: (167)
<223> OTHER INFORMATION: Xaa = ANY AMINO ACID

<400> SEQUENCE: 28

Glu Thr Val Met Tyr Pro Tyr Tyr Ser Lys Trp Ile Xaa Xaa His Arg
 1               5                  10                  15

Asp Leu Pro Leu Lys Leu Asn Gln Trp Cys Asn Val Val Xaa Trp Glu
             20                  25                  30

Phe Ser Asn Pro Thr Pro Xaa Ile Arg Ser Arg Glu Phe Leu Trp Gln
         35                  40                  45

Glu Gly His Thr Ala Phe Ala Thr Lys Asp Glu Ala Xaa Ala Glu Val
     50                  55                  60

Leu Glu Ile Leu Glu Leu Tyr Arg Arg Ile Tyr Glu Glu Tyr Leu Ala
 65                  70                  75                  80

Val Pro Val Ile Lys Gly Lys Xaa Ser Glu Leu Glu Lys Phe Ala Gly
                 85                  90                  95

Gly Leu Tyr Thr Xaa Asn Val Glu Ala Phe Ile Pro Asn Thr Gly Arg
            100                 105                 110

Gly Ile Gln Gly Ala Thr Ser His Cys Leu Gly Gln Asn Phe Ala Lys
        115                 120                 125

Met Phe Glu Ile Asn Phe Glu Asn Glu Lys Gly Glu Lys Ala Met Val
    130                 135                 140

Trp Gln Asn Ser Trp Ala Tyr Ser Thr Arg Thr Ile Gly Val Met Val
145                 150                 155                 160

Met Val His Gly Asp Asp Xaa Gly Ile Gly Thr Thr Ser
                165                 170

<210> SEQ ID NO 29
<211> LENGTH: 564
<212> TYPE: DNA
<213> ORGANISM: Triticum aestivum
<220> FEATURE:
<221> NAME/KEY: unsure
<222> LOCATION: (439)
<223> OTHER INFORMATION: n=a,c,g or t
<220> FEATURE:
<221> NAME/KEY: unsure
<222> LOCATION: (466)
<223> OTHER INFORMATION: n=a,c,g or t
<220> FEATURE:
<221> NAME/KEY: unsure
```

```
<222> LOCATION: (526)
<223> OTHER INFORMATION: n=a,c,g or t
<220> FEATURE:
<221> NAME/KEY: unsure
<222> LOCATION: (536)
<223> OTHER INFORMATION: n=a,c,g or t
<220> FEATURE:
<221> NAME/KEY: unsure
<222> LOCATION: (564)
<223> OTHER INFORMATION: n=a,c,g or t

<400> SEQUENCE: 29
tagcaatcca actcctttca taaggagccg tgaatttctt tggcaagaag gccatacagt     60
ttttgcaact aaagaggagg cagatgaaga ggtcctccaa atattggaac tctacaggag    120
aatatatgaa gaatttttag cagttccagt gtccaaaggg aggaaaagtg agatggaaaa    180
gtttgctggt ggactttata caaccagtgt agaggccttc attccaaata ctggccgtgg    240
tatacaaggt gcaacttcac attgtcttgg tcaaaacttt gcaaagatgt ttgatatcac    300
tttcgagaat gaaaagggtg aacggtccat ggtgtggcag aactcttggg catacactac    360
ccgctcgatt ggggtcatga taatgacaca tggtgatgac aagggcttag tgctgccacc    420
aaaggtgacc tatccaggnc attgtatcct gtgccattaa agatgntgac acaacagcta    480 ttaaagggc gtcgagcggc gttacacctt gaccaactgg atcggnagat ttgatnccgt    540
gaaatacccc caggtggaaa atcn                                           564

<210> SEQ ID NO 30
<211> LENGTH: 152
<212> TYPE: PRT
<213> ORGANISM: Triticum aestivum

<400> SEQUENCE: 30

Ser Asn Pro Thr Pro Phe Ile Arg Ser Arg Glu Phe Leu Trp Gln Glu
  1               5                  10                  15

Gly His Thr Val Phe Ala Thr Lys Glu Ala Asp Glu Glu Val Leu
             20                  25                  30

Gln Ile Leu Glu Leu Tyr Arg Arg Ile Tyr Glu Glu Phe Leu Ala Val
         35                  40                  45

Pro Val Ser Lys Gly Arg Lys Ser Glu Met Glu Lys Phe Ala Gly Gly
     50                  55                  60

Leu Tyr Thr Thr Ser Val Glu Ala Phe Ile Pro Asn Thr Gly Arg Gly
 65                  70                  75                  80

Ile Gln Gly Ala Thr Ser His Cys Leu Gly Gln Asn Phe Ala Lys Met
                 85                  90                  95

Phe Asp Ile Thr Phe Glu Asn Glu Lys Gly Glu Arg Ser Met Val Trp
            100                 105                 110

Gln Asn Ser Trp Ala Tyr Thr Thr Arg Ser Ile Gly Val Met Ile Met
        115                 120                 125

Thr His Gly Asp Asp Lys Gly Leu Val Leu Pro Pro Lys Val Thr Tyr
    130                 135                 140

Pro Gly His Cys Ile Leu Cys His
145                 150

<210> SEQ ID NO 31
<211> LENGTH: 1072
<212> TYPE: PRT
<213> ORGANISM: Saccharomyces cerevisiae

<400> SEQUENCE: 31
```

-continued

```
Met Ser Glu Ser Asn Ala His Phe Ser Phe Pro Lys Glu Glu Lys
 1               5                  10                  15

Val Leu Ser Leu Trp Asp Glu Ile Asp Ala Phe His Thr Ser Leu Glu
             20                  25                  30

Leu Thr Lys Asp Lys Pro Glu Phe Ser Phe Phe Asp Gly Pro Pro Phe
         35                  40                  45

Ala Thr Gly Thr Pro His Tyr Gly His Ile Leu Ala Ser Thr Ile Lys
     50                  55                  60

Asp Ile Val Pro Arg Tyr Ala Thr Met Thr Gly His His Val Glu Arg
 65                  70                  75                  80

Arg Phe Gly Trp Asp Thr His Gly Val Pro Ile Glu His Ile Ile Asp
                 85                  90                  95

Lys Lys Leu Gly Ile Thr Gly Lys Asp Asp Val Phe Lys Tyr Gly Leu
             100                 105                 110

Glu Asn Tyr Asn Asn Glu Cys Arg Ser Ile Val Met Thr Tyr Ala Ser
         115                 120                 125

Asp Trp Arg Lys Thr Ile Gly Arg Leu Gly Arg Trp Ile Asp Phe Asp
     130                 135                 140

Asn Asp Tyr Lys Thr Met Tyr Pro Ser Phe Met Glu Ser Thr Trp Trp
145                 150                 155                 160

Ala Phe Lys Gln Leu His Glu Lys Gly Gln Val Tyr Arg Gly Phe Lys
                165                 170                 175

Val Met Pro Tyr Ser Thr Gly Leu Thr Thr Pro Leu Ser Asn Phe Glu
             180                 185                 190

Ala Gln Gln Asn Tyr Lys Asp Val Asn Asp Pro Ala Val Thr Ile Gly
         195                 200                 205

Phe Asn Val Ile Gly Gln Glu Lys Thr Gln Leu Val Ala Trp Thr Thr
     210                 215                 220

Thr Pro Trp Thr Leu Pro Ser Asn Leu Ser Leu Cys Val Asn Ala Asp
225                 230                 235                 240

Phe Glu Tyr Val Lys Ile Tyr Asp Glu Thr Arg Asp Arg Tyr Phe Ile
                245                 250                 255

Leu Leu Glu Ser Leu Ile Lys Thr Leu Tyr Lys Lys Pro Lys Asn Glu
             260                 265                 270

Lys Tyr Lys Ile Val Glu Lys Ile Lys Gly Ser Asp Leu Val Gly Leu
         275                 280                 285

Lys Tyr Glu Pro Leu Phe Pro Tyr Phe Ala Glu Gln Phe His Glu Thr
     290                 295                 300

Ala Phe Arg Val Ile Ser Asp Asp Tyr Val Thr Ser Asp Ser Gly Thr
305                 310                 315                 320

Gly Ile Val His Asn Ala Pro Ala Phe Gly Glu Glu Asp Asn Ala Ala
                325                 330                 335

Cys Leu Lys Asn Gly Val Ile Ser Glu Asp Ser Val Leu Pro Asn Ala
             340                 345                 350

Ile Asp Asp Leu Gly Arg Phe Thr Lys Asp Val Pro Asp Phe Glu Gly
         355                 360                 365

Val Tyr Val Lys Asp Ala Asp Lys Leu Ile Ile Lys Tyr Leu Thr Asn
     370                 375                 380

Thr Gly Asn Leu Leu Leu Ala Ser Gln Ile Arg His Ser Tyr Pro Phe
385                 390                 395                 400

Cys Trp Arg Ser Asp Thr Pro Leu Leu Tyr Arg Ser Val Pro Ala Trp
                405                 410                 415

Phe Val Arg Val Lys Asn Ile Val Pro Gln Met Leu Asp Ser Val Met
```

-continued

```
                420                 425                 430
Lys Ser His Trp Val Pro Asn Thr Ile Lys Glu Lys Arg Phe Ala Asn
        435                 440                 445
Trp Ile Ala Asn Ala Arg Asp Trp Asn Val Ser Arg Asn Arg Tyr Trp
        450                 455                 460
Gly Thr Pro Ile Pro Leu Trp Val Ser Asp Asp Phe Glu Glu Val Val
465                 470                 475                 480
Cys Val Gly Ser Ile Lys Glu Leu Glu Glu Leu Thr Gly Val Arg Asn
                485                 490                 495
Ile Thr Asp Leu His Arg Asp Val Ile Asp Lys Leu Thr Ile Pro Ser
            500                 505                 510
Lys Gln Gly Lys Gly Asp Leu Lys Arg Ile Glu Glu Val Phe Asp Cys
        515                 520                 525
Trp Phe Glu Ser Gly Ser Met Pro Tyr Ala Ser Gln His Tyr Pro Phe
        530                 535                 540
Glu Asn Thr Glu Lys Phe Asp Glu Arg Val Pro Ala Asn Phe Ile Ser
545                 550                 555                 560
Glu Gly Leu Asp Gln Thr Arg Gly Trp Phe Tyr Thr Leu Ala Val Leu
                565                 570                 575
Gly Thr His Leu Phe Gly Ser Val Pro Tyr Lys Asn Val Ile Val Ser
            580                 585                 590
Gly Ile Val Leu Ala Ala Asp Gly Arg Lys Met Ser Lys Ser Leu Lys
        595                 600                 605
Asn Tyr Pro Asp Pro Ser Ile Val Leu Asn Lys Tyr Gly Ala Asp Ala
        610                 615                 620
Leu Arg Leu Tyr Leu Ile Asn Ser Pro Val Leu Lys Ala Glu Ser Leu
625                 630                 635                 640
Lys Phe Lys Glu Glu Gly Val Lys Glu Val Ser Lys Val Leu Leu
                645                 650                 655
Pro Trp Trp Asn Ser Phe Lys Phe Leu Asp Gly Gln Ile Ala Leu Leu
            660                 665                 670
Lys Lys Met Ser Asn Ile Asp Phe Gln Tyr Asp Asp Ser Val Lys Ser
        675                 680                 685
Asp Asn Val Met Asp Arg Trp Ile Leu Ala Ser Met Gln Ser Leu Val
        690                 695                 700
Gln Phe Ile His Glu Glu Met Gly Gln Tyr Lys Leu Tyr Thr Val Val
705                 710                 715                 720
Pro Lys Leu Leu Asn Phe Ile Asp Glu Leu Thr Asn Trp Tyr Ile Arg
                725                 730                 735
Phe Asn Arg Arg Arg Leu Lys Gly Glu Asn Gly Val Glu Asp Cys Leu
            740                 745                 750
Lys Ala Leu Asn Ser Leu Phe Asp Ala Leu Phe Thr Phe Val Arg Ala
        755                 760                 765
Met Ala Pro Phe Thr Pro Phe Leu Ser Glu Ser Ile Tyr Leu Arg Leu
        770                 775                 780
Lys Glu Tyr Ile Pro Glu Ala Val Leu Ala Lys Tyr Gly Lys Asp Gly
785                 790                 795                 800
Arg Ser Val His Phe Leu Ser Tyr Pro Val Val Lys Lys Glu Tyr Phe
                805                 810                 815
Asp Glu Ala Ile Glu Thr Ala Val Ser Arg Met Gln Ser Val Ile Asp
            820                 825                 830
Leu Gly Arg Asn Ile Arg Glu Lys Lys Thr Ile Ser Leu Lys Thr Pro
        835                 840                 845
```

-continued

```
Leu Lys Thr Leu Val Ile Leu His Ser Asp Glu Ser Tyr Leu Lys Asp
        850                 855                 860

Val Glu Ala Leu Lys Asn Tyr Ile Ile Glu Glu Leu Asn Val Arg Asp
865                 870                 875                 880

Val Val Ile Thr Ser Asp Glu Ala Lys Tyr Gly Val Glu Tyr Lys Ala
                885                 890                 895

Val Ala Asp Trp Pro Val Leu Gly Lys Leu Lys Lys Asp Ala Lys
            900                 905                 910

Lys Val Lys Asp Ala Leu Pro Ser Val Thr Ser Glu Gln Val Arg Glu
        915                 920                 925

Tyr Leu Glu Ser Gly Lys Leu Glu Val Ala Gly Ile Glu Leu Val Lys
    930                 935                 940

Gly Asp Leu Asn Ala Ile Arg Gly Leu Pro Glu Ser Ala Val Gln Ala
945                 950                 955                 960

Gly Gln Glu Thr Arg Thr Asp Gln Asp Val Leu Ile Ile Met Asp Thr
                965                 970                 975

Asn Ile Tyr Ser Glu Leu Lys Ser Glu Gly Leu Ala Arg Glu Leu Val
            980                 985                 990

Asn Arg Ile Gln Lys Leu Arg Lys Cys Gly Leu Glu Ala Thr Asp
        995                 1000                1005

Asp Val Leu Val Glu Tyr Glu Leu Val Lys Asp Thr Ile Asp Phe Glu
    1010                1015                1020

Ala Ile Val Lys Glu His Phe Asp Met Leu Ser Lys Thr Cys Arg Ser
1025                1030                1035                1040

Asp Ile Ala Lys Tyr Asp Gly Ser Lys Thr Asp Pro Ile Gly Asp Glu
                1045                1050                1055

Glu Gln Ser Ile Asn Asp Thr Ile Phe Lys Leu Lys Val Phe Lys Leu
            1060                1065                1070

<210> SEQ ID NO 32
<211> LENGTH: 1266
<212> TYPE: PRT
<213> ORGANISM: Homo sapiens

<400> SEQUENCE: 32

Met Ser Asn Lys Met Leu Gln Gln Val Pro Glu Asn Ile Asn Phe Pro
1               5                   10                  15

Ala Glu Glu Lys Ile Leu Glu Phe Trp Thr Glu Phe Asn Cys Phe
            20                  25                  30

Gln Glu Cys Leu Lys Gln Ser Lys His Lys Pro Lys Phe Thr Phe Tyr
        35                  40                  45

Asp Gly Pro Pro Phe Ala Thr Gly Leu Pro His Tyr Gly His Ile Leu
    50                  55                  60

Ala Gly Thr Ile Lys Asp Ile Val Thr Arg Tyr Ala His Gln Ser Gly
65                  70                  75                  80

Phe His Val Asp Arg Arg Phe Gly Trp Asp Cys His Gly Leu Pro Val
                85                  90                  95

Glu Tyr Glu Ile Asp Lys Thr Leu Gly Ile Arg Gly Pro Glu Asp Val
            100                 105                 110

Ala Lys Met Gly Ile Thr Glu Tyr Asn Asn Gln Cys Arg Ala Ile Val
        115                 120                 125

Met Arg Tyr Ser Ala Glu Trp Lys Ser Thr Val Ser Arg Leu Gly Arg
    130                 135                 140

Trp Ile Asp Phe Asp Asn Asp Tyr Lys Thr Leu Tyr Pro Gln Phe Met
```

-continued

```
                145                 150                 155                 160
        Glu Ser Val Trp Trp Val Phe Lys Gln Leu Tyr Asp Lys Gly Leu Val
                        165                 170                 175
        Tyr Arg Gly Val Lys Val Met Pro Phe Ser Thr Ala Cys Asn Thr Pro
                        180                 185                 190
        Leu Ser Asn Phe Glu Ser His Gln Asn Tyr Lys Asp Val Gln Asp Pro
                        195                 200                 205
        Ser Val Phe Val Thr Phe Pro Leu Glu Glu Asp Glu Thr Val Ser Leu
                210                 215                 220
        Val Ala Trp Thr Thr Thr Pro Trp Thr Leu Pro Ser Asn Leu Ala Val
        225                 230                 235                 240
        Cys Val Asn Pro Glu Met Gln Tyr Val Lys Ile Lys Asp Val Ala Arg
                        245                 250                 255
        Gly Arg Leu Leu Ile Leu Met Glu Ala Arg Leu Ser Ala Leu Tyr Lys
                        260                 265                 270
        Leu Glu Ser Asp Tyr Glu Ile Leu Glu Arg Phe Pro Gly Ala Tyr Leu
                        275                 280                 285
        Lys Gly Lys Lys Tyr Arg Pro Leu Phe Asp Tyr Phe Leu Lys Cys Lys
                290                 295                 300
        Glu Asn Gly Ala Phe Thr Val Leu Val Asp Asn Tyr Val Lys Glu Glu
        305                 310                 315                 320
        Glu Gly Thr Gly Val Val His Gln Ala Pro Tyr Phe Gly Ala Glu Asp
                        325                 330                 335
        Tyr Arg Val Cys Met Asp Phe Asn Ile Ile Arg Lys Asp Ser Leu Pro
                        340                 345                 350
        Val Cys Pro Val Asp Ala Ser Gly Cys Phe Thr Thr Glu Val Thr Asp
                        355                 360                 365
        Phe Ala Gly Gln Tyr Val Lys Asp Ala Asp Lys Ser Ile Ile Arg Thr
                        370                 375                 380
        Leu Lys Glu Gln Gly Arg Leu Leu Val Ala Thr Thr Phe Thr His Ser
        385                 390                 395                 400
        Tyr Pro Phe Cys Trp Arg Ser Asp Thr Pro Leu Ile Tyr Lys Ala Val
                        405                 410                 415
        Pro Ser Trp Phe Val Arg Val Glu Asn Met Val Asp Gln Leu Leu Arg
                        420                 425                 430
        Asn Asn Asp Leu Cys Tyr Trp Val Pro Glu Leu Val Arg Glu Lys Arg
                        435                 440                 445
        Phe Gly Asn Trp Leu Lys Asp Ala Arg Asp Trp Thr Ile Ser Arg Asn
                450                 455                 460
        Arg Tyr Trp Gly Thr Pro Ile Pro Leu Trp Val Ser Asp Asp Phe Glu
        465                 470                 475                 480
        Glu Val Val Cys Ile Gly Ser Val Ala Glu Leu Glu Glu Leu Ser Gly
                        485                 490                 495
        Ala Lys Ile Ser Asp Leu His Arg Glu Ser Val Asp His Leu Thr Ile
                        500                 505                 510
        Pro Ser Arg Cys Gly Lys Gly Ser Leu His Arg Ile Ser Glu Val Phe
                        515                 520                 525
        Asp Cys Trp Phe Glu Ser Gly Ser Met Pro Tyr Ala Gln Val His Tyr
                        530                 535                 540
        Pro Phe Glu Asn Lys Arg Glu Phe Glu Asp Ala Phe Pro Ala Asp Phe
        545                 550                 555                 560
        Ile Ala Glu Gly Ile Asp Gln Thr Arg Gly Trp Phe Tyr Thr Leu Leu
                        565                 570                 575
```

-continued

```
Val Leu Ala Thr Ala Leu Phe Gly Gln Pro Pro Phe Lys Asn Val Ile
            580                 585                 590

Val Asn Gly Leu Val Leu Ala Ser Asp Gly Gln Lys Met Ser Lys Arg
            595                 600                 605

Lys Lys Asn Tyr Pro Asp Pro Val Ser Ile Ile Gln Lys Tyr Gly Ala
            610                 615                 620

Asp Ala Leu Arg Leu Tyr Leu Ile Asn Ser Pro Val Val Arg Ala Glu
625                 630                 635                 640

Asn Leu Arg Phe Lys Glu Gly Val Arg Asp Val Leu Lys Asp Val
            645                 650                 655

Leu Leu Pro Trp Tyr Asn Ala Tyr Arg Phe Leu Ile Gln Asn Val Leu
            660                 665                 670

Arg Leu Gln Lys Glu Glu Ile Glu Phe Leu Tyr Asn Glu Asn Thr
            675                 680                 685

Val Arg Glu Ser Pro Asn Ile Thr Asp Arg Trp Ile Leu Ser Phe Met
            690                 695                 700

Gln Ser Leu Ile Gly Phe Phe Glu Thr Glu Met Ala Ala Tyr Arg Leu
705                 710                 715                 720

Tyr Thr Val Val Pro Arg Leu Val Lys Phe Val Asp Ile Leu Thr Asn
            725                 730                 735

Trp Tyr Val Arg Met Asn Arg Arg Leu Lys Gly Glu Asn Gly Met
            740                 745                 750

Glu Asp Cys Val Met Ala Leu Glu Thr Leu Phe Ser Val Leu Leu Ser
            755                 760                 765

Leu Cys Arg Leu Met Ala Pro Tyr Thr Pro Phe Leu Thr Glu Leu Met
770                 775                 780

Tyr Gln Asn Leu Lys Val Leu Ile Asp Pro Val Ser Val Gln Asp Lys
785                 790                 795                 800

Asp Thr Leu Ser Ile His Tyr Leu Met Leu Pro Arg Val Arg Glu Glu
            805                 810                 815

Leu Ile Asp Lys Lys Thr Glu Ser Ala Val Ser Gln Met Gln Ser Val
            820                 825                 830

Ile Glu Leu Gly Arg Val Ile Arg Asp Arg Lys Thr Ile Pro Ile Lys
            835                 840                 845

Tyr Pro Leu Lys Glu Ile Val Ile His Gln Asp Pro Glu Ala Leu
            850                 855                 860

Lys Asp Ile Lys Ser Leu Glu Lys Tyr Ile Ile Glu Glu Leu Asn Val
865                 870                 875                 880

Arg Lys Val Thr Leu Ser Thr Asp Lys Asn Lys Tyr Gly Ile Arg Leu
            885                 890                 895

Arg Ala Glu Pro Asp His Met Val Leu Gly Lys Arg Leu Lys Gly Ala
            900                 905                 910

Phe Lys Ala Val Met Thr Ser Ile Lys Gln Leu Ser Ser Glu Glu Leu
            915                 920                 925

Glu Gln Phe Gln Lys Thr Gly Thr Ile Val Val Glu Gly His Glu Leu
930                 935                 940

His Asp Glu Asp Ile Arg Leu Met Tyr Thr Phe Asp Gln Ala Thr Gly
945                 950                 955                 960

Gly Thr Ala Gln Phe Glu Ala His Ser Asp Ala Gln Ala Leu Val Leu
            965                 970                 975

Leu Asp Val Thr Pro Asp Gln Ser Met Val Asp Glu Gly Met Ala Arg
            980                 985                 990
```

```
Glu Val Ile Asn Arg Ile Gln Lys Leu Arg Lys Lys Cys Asn Leu Val
        995                 1000                1005

Pro Thr Asp Glu Ile Thr Val Tyr Tyr Lys Ala Lys Ser Glu Gly Thr
    1010                1015                1020

Tyr Leu Asn Ser Val Ile Glu Ser His Thr Glu Phe Ile Phe Thr Thr
1025                1030                1035                1040

Ile Lys Ala Pro Leu Lys Pro Tyr Pro Val Ser Pro Ser Asp Lys Val
            1045                1050                1055

Leu Ile Gln Glu Lys Thr Gln Leu Lys Gly Ser Glu Leu Glu Ile Thr
        1060                1065                1070

Leu Thr Arg Gly Ser Ser Leu Pro Gly Pro Ala Cys Ala Tyr Val Asn
    1075                1080                1085

Leu Asn Ile Cys Ala Asn Gly Ser Glu Gln Gly Gly Val Leu Leu Leu
1090                1095                1100

Glu Asn Pro Lys Gly Asp Asn Arg Leu Asp Leu Leu Lys Leu Lys Ser
            1105                1110                1115                1120

Val Val Thr Ser Ile Phe Gly Val Lys Asn Thr Glu Leu Ala Val Phe
        1125                1130                1135

His Asp Glu Thr Glu Ile Gln Asn Gln Thr Asp Leu Leu Ser Leu Ser
    1140                1145                1150

Gly Lys Thr Leu Cys Val Thr Ala Gly Ser Ala Pro Ser Leu Ile Asn
1155                1160                1165

Ser Ser Ser Thr Leu Leu Cys Gln Tyr Ile Asn Leu Gln Leu Leu Asn
            1170                1175                1180

Ala Lys Pro Gln Glu Cys Leu Met Gly Thr Val Gly Thr Leu Leu Leu
1185                1190                1195                1200

Glu Asn Pro Leu Gly Gln Asn Gly Leu Thr His Gln Gly Leu Leu Tyr
            1205                1210                1215

Glu Ala Ala Lys Val Phe Gly Leu Arg Ser Arg Lys Leu Lys Leu Phe
        1220                1225                1230

Leu Asn Glu Thr Gln Thr Gln Glu Ile Thr Glu Asp Ile Pro Val Lys
    1235                1240                1245

Thr Leu Asn Met Lys Thr Val Tyr Val Ser Val Leu Pro Thr Thr Ala
    1250                1255                1260

Asp Phe
1265

<210> SEQ ID NO 33
<211> LENGTH: 1262
<212> TYPE: PRT
<213> ORGANISM: Homo sapiens

<400> SEQUENCE: 33

Met Leu Gln Gln Val Pro Glu Asn Ile Asn Phe Pro Ala Glu Glu Glu
1               5                   10                  15

Lys Ile Leu Glu Phe Trp Thr Glu Phe Asn Cys Phe Gln Glu Cys Leu
            20                  25                  30

Lys Gln Ser Lys His Lys Pro Lys Phe Thr Phe Tyr Asp Gly Pro Pro
        35                  40                  45

Phe Ala Thr Gly Leu Pro His Tyr Gly His Ile Leu Ala Gly Thr Ile
    50                  55                  60

Lys Asp Ile Val Thr Arg Tyr Ala His Gln Ser Gly Phe His Val Asp
65                  70                  75                  80

Arg Arg Phe Gly Trp Asp Cys His Gly Leu Pro Val Glu Tyr Glu Ile
            85                  90                  95
```

```
Asp Lys Thr Leu Gly Ile Arg Gly Pro Glu Asp Val Ala Lys Met Gly
            100                 105                 110
Ile Thr Glu Tyr Asn Asn Gln Cys Arg Ala Ile Val Met Arg Tyr Ser
        115                 120                 125
Ala Glu Trp Lys Ser Thr Val Ser Arg Leu Gly Arg Trp Ile Asp Phe
    130                 135                 140
Asp Asn Asp Tyr Lys Thr Leu Tyr Pro Gln Phe Met Glu Ser Val Trp
145                 150                 155                 160
Trp Val Phe Lys Gln Leu Tyr Asp Lys Gly Leu Val Tyr Arg Gly Val
                165                 170                 175
Lys Val Met Pro Phe Ser Thr Ala Cys Asn Thr Pro Leu Ser Asn Phe
            180                 185                 190
Glu Ser His Gln Asn Tyr Lys Asp Val Gln Asp Pro Ser Val Phe Val
        195                 200                 205
Thr Phe Pro Leu Glu Glu Asp Glu Thr Val Ser Leu Val Ala Trp Thr
    210                 215                 220
Thr Thr Pro Trp Thr Leu Pro Ser Asn Leu Ala Val Cys Val Asn Pro
225                 230                 235                 240
Glu Met Gln Tyr Val Lys Ile Lys Asp Val Ala Arg Gly Arg Leu Leu
                245                 250                 255
Ile Leu Met Glu Ala Arg Leu Ser Ala Leu Tyr Lys Leu Glu Ser Asp
            260                 265                 270
Tyr Glu Ile Leu Glu Arg Phe Pro Gly Ala Tyr Leu Lys Gly Lys Lys
        275                 280                 285
Tyr Arg Pro Leu Phe Asp Tyr Phe Leu Lys Cys Lys Glu Asn Gly Ala
    290                 295                 300
Phe Thr Val Leu Val Asp Asn Tyr Val Lys Glu Glu Gly Thr Gly
305                 310                 315                 320
Val Val His Gln Ala Pro Tyr Phe Gly Ala Glu Asp Tyr Arg Val Cys
                325                 330                 335
Met Asp Phe Asn Ile Ile Arg Lys Asp Ser Leu Pro Val Cys Pro Val
            340                 345                 350
Asp Ala Ser Gly Cys Phe Thr Thr Glu Val Thr Asp Phe Ala Gly Gln
        355                 360                 365
Tyr Val Lys Asp Ala Asp Lys Ser Ile Ile Arg Thr Leu Lys Glu Gln
    370                 375                 380
Gly Arg Leu Leu Val Ala Thr Thr Phe Thr His Ser Tyr Pro Phe Cys
385                 390                 395                 400
Trp Arg Ser Asp Thr Pro Leu Ile Tyr Lys Ala Val Pro Ser Trp Phe
                405                 410                 415
Val Arg Val Glu Asn Met Val Asp Gln Leu Leu Arg Asn Asn Asp Leu
            420                 425                 430
Cys Tyr Trp Val Pro Glu Leu Val Arg Glu Lys Arg Phe Gly Asn Trp
        435                 440                 445
Leu Lys Asp Ala Arg Asp Trp Thr Ile Ser Arg Asn Arg Tyr Trp Gly
    450                 455                 460
Thr Pro Ile Pro Leu Trp Val Ser Asp Asp Phe Glu Glu Val Val Cys
465                 470                 475                 480
Ile Gly Ser Val Ala Glu Leu Glu Glu Leu Ser Gly Ala Lys Ile Ser
                485                 490                 495
Asp Leu His Arg Glu Ser Val Asp His Leu Thr Ile Pro Ser Arg Cys
            500                 505                 510
```

```
Gly Lys Gly Ser Leu His Arg Ile Ser Glu Val Phe Asp Cys Trp Phe
        515                 520                 525
Glu Ser Gly Ser Met Pro Tyr Ala Gln Val His Tyr Pro Phe Glu Asn
        530                 535                 540
Lys Arg Glu Phe Glu Asp Ala Phe Pro Ala Asp Phe Ile Ala Glu Gly
545                 550                 555                 560
Ile Asp Gln Thr Arg Gly Trp Phe Tyr Thr Leu Leu Val Leu Ala Thr
                565                 570                 575
Ala Leu Phe Gly Gln Pro Pro Phe Lys Asn Val Ile Val Asn Gly Leu
            580                 585                 590
Val Leu Ala Ser Asp Gly Gln Lys Met Ser Lys Arg Lys Lys Asn Tyr
        595                 600                 605
Pro Asp Pro Val Ser Ile Ile Gln Lys Tyr Gly Ala Asp Ala Leu Arg
610                 615                 620
Leu Tyr Leu Ile Asn Ser Pro Val Val Arg Ala Glu Asn Leu Arg Phe
625                 630                 635                 640
Lys Glu Glu Gly Val Arg Asp Val Leu Lys Asp Val Leu Leu Pro Trp
                645                 650                 655
Tyr Asn Ala Tyr Arg Phe Leu Ile Gln Asn Val Leu Arg Leu Gln Lys
            660                 665                 670
Glu Glu Glu Ile Glu Phe Leu Tyr Asn Glu Asn Thr Val Arg Glu Ser
        675                 680                 685
Pro Asn Ile Thr Asp Arg Trp Ile Leu Ser Phe Met Gln Ser Leu Ile
        690                 695                 700
Gly Phe Phe Glu Thr Glu Met Ala Ala Tyr Arg Leu Tyr Thr Val Val
705                 710                 715                 720
Pro Arg Leu Val Lys Phe Val Asp Ile Leu Thr Asn Trp Tyr Val Arg
                725                 730                 735
Met Asn Arg Arg Arg Leu Lys Gly Glu Asn Gly Met Glu Asp Cys Val
            740                 745                 750
Met Ala Leu Glu Thr Leu Phe Ser Val Leu Leu Ser Leu Cys Arg Leu
        755                 760                 765
Ile Ala Pro Tyr Thr Pro Phe Leu Thr Glu Leu Met Tyr Gln Asn Leu
        770                 775                 780
Lys Val Leu Ile Asp Pro Val Ser Val Gln Asp Lys Asp Thr Leu Ser
785                 790                 795                 800
Ile His Tyr Leu Met Leu Pro Arg Val Arg Glu Leu Ile Asp Lys
                805                 810                 815
Lys Thr Glu Ser Ala Val Ser Gln Met Gln Ser Val Ile Glu Leu Gly
            820                 825                 830
Arg Val Ile Arg Asp Arg Lys Thr Ile Pro Ile Lys Tyr Pro Leu Lys
        835                 840                 845
Glu Ile Val Val Ile His Gln Asp Pro Glu Ala Leu Lys Asp Ile Lys
850                 855                 860
Ser Leu Glu Lys Tyr Ile Ile Glu Glu Leu Asn Val Arg Lys Val Thr
865                 870                 875                 880
Leu Ser Thr Asp Lys Asn Lys Tyr Gly Ile Arg Leu Arg Ala Glu Pro
                885                 890                 895
Asp His Met Val Leu Gly Lys Arg Leu Lys Gly Ala Phe Lys Ala Val
            900                 905                 910
Met Thr Ser Ile Lys Gln Leu Ser Ser Glu Leu Glu Gln Phe Gln
        915                 920                 925
Lys Thr Gly Thr Ile Val Val Glu Gly His Glu Leu His Asp Glu Asp
```

-continued

```
            930                 935                 940
Ile Arg Leu Met Tyr Thr Phe Asp Gln Ala Thr Gly Gly Thr Ala Gln
945                 950                 955                 960

Phe Glu Ala His Ser Asp Ala Gln Ala Leu Val Leu Asp Val Thr
                965                 970                 975

Pro Asp Gln Ser Met Val Asp Glu Gly Met Ala Arg Glu Val Ile Asn
            980                 985                 990

Arg Ile Gln Lys Leu Arg Lys Lys Cys Asn Leu Val Pro Thr Asp Glu
            995                 1000                1005

Ile Thr Val Tyr Tyr Lys Ala Lys Ser Glu Gly Thr Tyr Leu Asn Ser
    1010                1015                1020

Val Ile Glu Ser His Thr Glu Phe Ile Phe Thr Thr Ile Lys Ala Pro
1025                1030                1035                1040

Leu Lys Pro Tyr Pro Val Ser Pro Ser Asp Lys Val Leu Ile Gln Glu
                1045                1050                1055

Lys Thr Gln Leu Lys Gly Ser Glu Leu Glu Ile Thr Leu Thr Arg Gly
            1060                1065                1070

Ser Ser Leu Pro Gly Pro Ala Cys Ala Tyr Val Asn Leu Asn Ile Cys
    1075                1080                1085

Ala Asn Gly Ser Glu Gln Gly Gly Val Leu Leu Glu Asn Pro Lys
1090                1095                1100

Gly Asp Asn Arg Leu Asp Leu Leu Lys Leu Lys Ser Val Val Thr Ser
1105                1110                1115                1120

Ile Phe Gly Val Lys Asn Thr Glu Leu Ala Val Phe His Asp Glu Thr
                1125                1130                1135

Glu Ile Gln Asn Gln Thr Asp Leu Leu Ser Leu Ser Gly Lys Thr Leu
            1140                1145                1150

Cys Val Thr Ala Gly Ser Ala Pro Ser Leu Ile Asn Ser Ser Ser Thr
    1155                1160                1165

Leu Leu Cys Gln Tyr Ile Asn Leu Gln Leu Leu Asn Ala Lys Pro Gln
    1170                1175                1180

Glu Cys Leu Met Gly Thr Val Gly Thr Leu Leu Leu Glu Asn Pro Leu
1185                1190                1195                1200

Gly Gln Asn Gly Leu Thr His Gln Gly Leu Leu Tyr Glu Ala Ala Lys
            1205                1210                1215

Val Phe Gly Leu Arg Ser Arg Lys Leu Lys Leu Phe Leu Asn Glu Thr
            1220                1225                1230

Gln Thr Gln Glu Ile Thr Glu Asp Ile Pro Val Lys Thr Leu Asn Met
    1235                1240                1245

Lys Thr Val Tyr Val Ser Val Leu Pro Thr Thr Ala Asp Phe
    1250                1255                1260

<210> SEQ ID NO 34
<211> LENGTH: 626
<212> TYPE: PRT
<213> ORGANISM: Arabidopsis thaliana

<400> SEQUENCE: 34

Met Glu Gly Ala Ala Asp Gln Thr Thr Lys Ala Leu Ser Glu Leu Ala
1                5                  10                  15

Met Asp Ser Ser Thr Thr Leu Asn Ala Ala Glu Ser Ser Ala Gly Asp
            20                  25                  30

Gly Ala Gly Pro Arg Ser Lys Asn Ala Leu Lys Lys Glu Gln Lys Met
        35                  40                  45
```

-continued

```
Lys Gln Lys Glu Glu Lys Arg Arg Lys Asp Glu Glu Lys Ala Glu
 50                  55                  60

Lys Ala Lys Gln Ala Pro Lys Ala Ser Ser Gln Lys Ala Val Ala Ala
 65                  70                  75                  80

Asp Asp Glu Glu Met Asp Ala Thr Gln Tyr Tyr Glu Asn Arg Leu Lys
                     85                  90                  95

Tyr Leu Ala Ala Glu Lys Ala Lys Gly Glu Asn Pro Tyr Pro His Lys
                100                 105                 110

Phe Ala Val Ser Met Ser Ile Pro Lys Tyr Ile Glu Thr Tyr Gly Ser
                115                 120                 125

Leu Asn Asn Gly Asp His Val Glu Asn Ala Glu Glu Ser Leu Ala Gly
                130                 135                 140

Arg Ile Met Ser Lys Arg Ser Ser Ser Lys Leu Phe Phe Tyr Asp
145                 150                 155                 160

Leu His Gly Asp Asp Phe Lys Val Gln Val Met Ala Asp Ala Ser Lys
                165                 170                 175

Ser Gly Leu Asp Glu Ala Glu Phe Leu Lys Leu His Ser Asn Ala Lys
                180                 185                 190

Arg Gly Asp Ile Val Gly Val Ile Gly Phe Pro Gly Lys Thr Lys Arg
                195                 200                 205

Gly Glu Leu Ser Ile Phe Pro Arg Ser Phe Ile Leu Leu Ser His Cys
                210                 215                 220

Leu His Met Met Pro Arg Lys Ala Asp Asn Val Asn Ala Lys Lys Pro
225                 230                 235                 240

Glu Ile Trp Val Pro Gly Gln Thr Arg Asn Pro Glu Ala Tyr Val Leu
                245                 250                 255

Lys Asp Gln Glu Ser Arg Tyr Arg Gln Arg His Leu Asp Met Ile Leu
                260                 265                 270

Asn Val Glu Val Arg Gln Ile Phe Arg Thr Arg Ala Lys Ile Ile Ser
                275                 280                 285

Tyr Val Arg Arg Phe Leu Asp Asn Lys Asn Phe Leu Glu Val Glu Thr
                290                 295                 300

Pro Met Met Asn Met Ile Ala Gly Gly Ala Ala Ala Arg Pro Phe Val
305                 310                 315                 320

Thr His His Asn Asp Leu Asp Met Arg Leu Tyr Met Arg Ile Ala Pro
                325                 330                 335

Glu Leu Tyr Leu Lys Gln Leu Ile Val Gly Gly Leu Glu Arg Val Tyr
                340                 345                 350

Glu Ile Gly Lys Gln Phe Arg Asn Glu Gly Ile Asp Leu Thr His Asn
                355                 360                 365

Pro Glu Phe Thr Thr Cys Glu Phe Tyr Met Ala Phe Ala Asp Tyr Asn
                370                 375                 380

Asp Leu Met Glu Met Thr Glu Val Met Leu Ser Gly Met Val Lys Glu
385                 390                 395                 400

Leu Thr Gly Gly Tyr Lys Ile Lys Tyr Asn Ala Asn Gly Tyr Asp Lys
                405                 410                 415

Asp Pro Ile Glu Ile Asp Phe Thr Pro Phe Arg Arg Ile Glu Met
                420                 425                 430

Ile Gly Glu Leu Glu Lys Val Ala Lys Leu Asn Ile Pro Lys Asp Leu
                435                 440                 445

Ala Ser Glu Glu Ala Asn Lys Tyr Leu Ile Asp Ala Cys Ala Arg Phe
450                 455                 460

Asp Val Lys Cys Pro Pro Pro Gln Thr Thr Ala Arg Leu Leu Asp Lys
```

```
                465                 470                 475                 480
Leu Val Gly Glu Phe Leu Glu Pro Thr Cys Val Asn Pro Thr Phe Ile
                    485                 490                 495

Ile Asn Gln Pro Glu Ile Met Ser Pro Leu Ala Lys Trp His Arg Ser
            500                 505                 510

Lys Ser Gly Leu Thr Glu Arg Phe Glu Leu Phe Ile Asn Lys His Glu
        515                 520                 525

Leu Cys Asn Ala Tyr Thr Glu Leu Asn Asp Pro Val Val Gln Arg Gln
    530                 535                 540

Arg Phe Ala Asp Gln Leu Lys Asp Arg Gln Ser Gly Asp Asp Glu Ala
545                 550                 555                 560

Met Ala Leu Asp Glu Thr Phe Cys Asn Ala Leu Glu Tyr Gly Leu Ala
                565                 570                 575

Pro Thr Gly Gly Trp Gly Leu Gly Ile Asp Arg Leu Ser Met Leu Leu
            580                 585                 590

Thr Asp Ser Leu Asn Ile Lys Glu Val Leu Phe Phe Pro Ala Met Arg
        595                 600                 605

Pro Pro Gln Glu Glu Ser Ala Ala Ala Gln Ala Pro Leu Thr Glu Glu
    610                 615                 620

Lys Lys
625

<210> SEQ ID NO 35
<211> LENGTH: 451
<212> TYPE: PRT
<213> ORGANISM: Homo sapiens

<400> SEQUENCE: 35

Met Val Gly Ser Ala Leu Arg Arg Gly Ala His Ala Tyr Val Tyr Leu
1               5                   10                  15

Val Ser Lys Ala Ser His Ile Ser Arg Gly His Gln His Gln Ala Trp
            20                  25                  30

Gly Ser Arg Pro Pro Ala Ala Glu Cys Ala Thr Gln Arg Ala Pro Gly
        35                  40                  45

Ser Val Val Glu Leu Leu Gly Lys Ser Tyr Pro Gln Asp Asp His Ser
    50                  55                  60

Asn Leu Thr Arg Lys Val Leu Thr Arg Val Gly Arg Asn Leu His Asn
65                  70                  75                  80

Gln Gln His His Pro Leu Trp Leu Ile Lys Glu Arg Val Lys Glu His
                85                  90                  95

Phe Tyr Lys Gln Tyr Val Gly Arg Phe Gly Thr Pro Leu Phe Ser Val
            100                 105                 110

Tyr Asp Asn Leu Ser Pro Val Val Thr Thr Trp Gln Asn Phe Asp Ser
        115                 120                 125

Leu Leu Ile Pro Ala Asp His Pro Ser Arg Lys Lys Gly Asp Asn Tyr
    130                 135                 140

Tyr Leu Asn Arg Thr His Met Leu Arg Ala His Thr Ser Ala His Gln
145                 150                 155                 160

Trp Asp Leu Leu His Ala Gly Leu Asp Ala Phe Leu Val Val Gly Asp
                165                 170                 175

Val Tyr Arg Arg Asp Gln Ile Asp Ser Gln His Tyr Pro Ile Phe His
            180                 185                 190

Gln Leu Glu Ala Val Arg Leu Phe Ser Lys His Glu Leu Phe Ala Gly
        195                 200                 205
```

```
Ile Lys Asp Gly Glu Ser Leu Gln Leu Phe Glu Gln Ser Ser Arg Ser
210                 215                 220

Ala His Lys Gln Glu Thr His Thr Met Glu Ala Val Lys Leu Val Glu
225                 230                 235                 240

Phe Asp Leu Lys Gln Thr Leu Thr Arg Leu Met Ala His Leu Phe Gly
            245                 250                 255

Asp Glu Leu Glu Ile Arg Trp Val Asp Cys Tyr Phe Pro Phe Thr His
            260                 265                 270

Pro Ser Phe Glu Met Glu Ile Asn Phe His Gly Glu Trp Leu Glu Val
            275                 280                 285

Leu Gly Cys Gly Val Met Glu Gln Leu Val Asn Ser Ala Gly Ala
290                 295                 300

Gln Asp Arg Ile Gly Trp Ala Phe Gly Leu Gly Leu Glu Arg Leu Ala
305                 310                 315                 320

Met Ile Leu Tyr Asp Ile Pro Asp Ile Arg Leu Phe Trp Cys Glu Asp
            325                 330                 335

Glu Arg Phe Leu Lys Gln Phe Cys Val Ser Asn Ile Asn Gln Lys Val
            340                 345                 350

Lys Phe Gln Pro Leu Ser Lys Tyr Pro Ala Val Ile Asn Asp Ile Ser
            355                 360                 365

Phe Trp Leu Pro Ser Glu Asn Tyr Ala Glu Asn Asp Phe Tyr Asp Leu
370                 375                 380

Val Arg Thr Ile Gly Gly Asp Leu Val Glu Lys Val Asp Leu Ile Asp
385                 390                 395                 400

Lys Phe Val His Pro Lys Thr His Lys Thr Ser His Cys Tyr Arg Ile
            405                 410                 415

Thr Tyr Arg His Met Glu Arg Thr Leu Ser Gln Arg Glu Val Arg His
            420                 425                 430

Ile His Gln Ala Leu Gln Glu Ala Ala Val Gln Leu Leu Gly Val Glu
            435                 440                 445

Gly Arg Phe
450

<210> SEQ ID NO 36
<211> LENGTH: 503
<212> TYPE: PRT
<213> ORGANISM: Saccharomyces cerevisiae

<400> SEQUENCE: 36

Met Ser Asp Phe Gln Leu Glu Ile Leu Lys Lys Leu Asp Glu Leu Asp
1               5                   10                  15

Glu Ile Lys Ser Thr Leu Ala Thr Phe Pro Gln His Gly Ser Gln Asp
                20                  25                  30

Val Leu Ser Ala Leu Asn Ser Leu Lys Ala His Asn Lys Leu Glu Phe
            35                  40                  45

Ser Lys Val Asp Thr Val Thr Tyr Asp Leu Thr Lys Glu Gly Ala Gln
        50                  55                  60

Ile Leu Asn Glu Gly Ser Tyr Glu Ile Lys Leu Val Lys Leu Ile Gln
65                  70                  75                  80

Glu Leu Gly Gln Leu Gln Ile Lys Asp Val Met Ser Lys Leu Gly Pro
                85                  90                  95

Gln Val Gly Lys Val Gly Gln Ala Arg Ala Phe Lys Asn Gly Trp Ile
            100                 105                 110

Ala Lys Asn Ala Ser Asn Glu Leu Glu Leu Ser Ala Lys Leu Gln Asn
        115                 120                 125
```

```
Thr Asp Leu Asn Glu Leu Thr Asp Glu Thr Gln Ser Ile Leu Ala Gln
    130                 135                 140

Ile Lys Asn Asn Ser His Leu Asp Ser Ile Asp Ala Lys Ile Leu Asn
145                 150                 155                 160

Asp Leu Lys Lys Arg Lys Leu Ile Ala Gln Gly Lys Ile Thr Asp Phe
                165                 170                 175

Ser Val Thr Lys Gly Pro Glu Phe Ser Thr Asp Leu Thr Lys Leu Glu
            180                 185                 190

Thr Asp Leu Thr Ser Asp Met Val Ser Thr Asn Ala Tyr Lys Asp Leu
        195                 200                 205

Lys Phe Lys Pro Tyr Asn Phe Asn Ser Gln Gly Val Gln Ile Ser Ser
210                 215                 220

Gly Ala Leu His Pro Leu Asn Lys Val Arg Glu Glu Phe Arg Gln Ile
225                 230                 235                 240

Phe Phe Ser Met Gly Phe Thr Glu Met Pro Ser Asn Gln Tyr Val Glu
                245                 250                 255

Thr Gly Phe Trp Asn Phe Asp Ala Leu Tyr Val Pro Gln Gln His Pro
            260                 265                 270

Ala Arg Asp Leu Gln Asp Thr Phe Tyr Ile Lys Asp Pro Leu Thr Ala
        275                 280                 285

Glu Leu Pro Asp Asp Lys Thr Tyr Met Asp Asn Ile Lys Ala Val His
    290                 295                 300

Glu Gln Gly Arg Phe Gly Ser Ile Gly Tyr Arg Tyr Asn Trp Lys Pro
305                 310                 315                 320

Glu Glu Cys Gln Lys Leu Val Leu Arg Thr His Ser Thr Ala Ile Ser
                325                 330                 335

Ala Arg Met Leu His Asp Leu Ala Lys Asp Pro Lys Pro Thr Arg Leu
            340                 345                 350

Phe Ser Ile Asp Arg Val Phe Arg Asn Glu Ala Val Asp Ala Thr His
        355                 360                 365

Leu Ala Glu Phe His Gln Val Glu Gly Val Leu Ala Asp Tyr Asn Ile
    370                 375                 380

Thr Leu Gly Asp Leu Ile Lys Phe Met Glu Glu Phe Phe Glu Arg Met
385                 390                 395                 400

Gly Val Thr Gly Leu Arg Phe Lys Pro Thr Tyr Asn Pro Tyr Thr Glu
                405                 410                 415

Pro Ser Met Glu Ile Phe Ser Trp His Glu Gly Leu Gln Lys Trp Val
            420                 425                 430

Glu Ile Gly Asn Ser Gly Met Phe Arg Pro Glu Met Leu Glu Ser Met
        435                 440                 445

Gly Leu Pro Lys Asp Leu Arg Val Leu Gly Trp Gly Leu Ser Leu Glu
    450                 455                 460

Arg Pro Thr Met Ile Lys Tyr Lys Val Gln Asn Ile Arg Glu Leu Leu
465                 470                 475                 480

Gly His Lys Val Ser Leu Asp Phe Ile Glu Thr Asn Pro Ala Ala Arg
                485                 490                 495

Leu Asp Glu Asp Leu Tyr Glu
            500

<210> SEQ ID NO 37
<211> LENGTH: 1440
<212> TYPE: PRT
<213> ORGANISM: Homo sapiens
```

<400> SEQUENCE: 37

```
Met Glu His Thr Glu Ile Asp His Trp Leu Glu Phe Ser Ala Thr Lys
  1               5                  10                  15

Leu Ser Ser Cys Asp Ser Phe Thr Ser Thr Ile Asn Glu Leu Asn His
             20                  25                  30

Cys Leu Ser Leu Arg Thr Tyr Leu Val Gly Asn Ser Leu Ser Leu Ala
         35                  40                  45

Asp Leu Cys Val Trp Ala Thr Leu Lys Gly Asn Ala Ala Trp Gln Glu
     50                  55                  60

Gln Leu Lys Gln Lys Lys Ala Pro Val His Val Lys Arg Trp Phe Gly
 65                  70                  75                  80

Phe Leu Glu Ala Gln Gln Ala Phe Gln Ser Val Gly Thr Lys Trp Asp
                 85                  90                  95

Val Ser Thr Thr Lys Ala Arg Val Ala Pro Glu Lys Lys Gln Asp Val
            100                 105                 110

Gly Lys Phe Val Glu Leu Pro Gly Ala Glu Met Gly Lys Val Thr Val
        115                 120                 125

Arg Phe Pro Pro Glu Ala Ser Gly Tyr Leu His Ile Gly His Ala Lys
130                 135                 140

Ala Ala Leu Leu Asn Gln His Tyr Gln Val Asn Phe Lys Gly Lys Leu
145                 150                 155                 160

Ile Met Arg Phe Asp Asp Thr Asn Pro Glu Lys Lys Glu Asp Phe
                165                 170                 175

Glu Lys Val Ile Leu Glu Asp Val Ala Met Leu His Ile Lys Pro Asp
                180                 185                 190

Gln Phe Thr Tyr Thr Ser Asp His Phe Glu Thr Ile Met Lys Tyr Ala
            195                 200                 205

Glu Lys Leu Ile Gln Glu Gly Lys Ala Tyr Val Asp Asp Thr Pro Ala
        210                 215                 220

Glu Gln Met Lys Ala Glu Arg Glu Gln Arg Ile Glu Ser Lys His Arg
225                 230                 235                 240

Lys Asn Pro Ile Glu Lys Asn Leu Gln Met Trp Glu Glu Met Lys Lys
                245                 250                 255

Gly Ser Gln Phe Gly His Ser Cys Cys Leu Arg Ala Lys Ile Asp Met
            260                 265                 270

Ser Ser Asn Asn Gly Cys Met Arg Asp Pro Thr Leu Tyr Arg Cys Lys
        275                 280                 285

Ile Gln Pro His Pro Arg Thr Gly Asn Lys Tyr Asn Val Tyr Pro Thr
    290                 295                 300

Tyr Asp Phe Ala Cys Pro Ile Val Asp Ser Ile Glu Gly Val Thr His
305                 310                 315                 320

Ala Leu Arg Thr Thr Glu Tyr His Asp Arg Asp Glu Gln Phe Tyr Trp
                325                 330                 335

Ile Ile Glu Ala Leu Gly Ile Arg Lys Pro Tyr Ile Trp Glu Tyr Ser
            340                 345                 350

Arg Leu Asn Leu Asn Asn Thr Val Leu Ser Lys Arg Lys Leu Thr Trp
        355                 360                 365

Phe Val Asn Glu Gly Leu Val Asp Gly Trp Asp Asp Pro Arg Phe Pro
    370                 375                 380

Thr Val Arg Gly Val Leu Arg Arg Gly Met Thr Val Glu Gly Leu Lys
385                 390                 395                 400

Gln Phe Ile Ala Ala Gln Gly Ser Ser Arg Ser Val Val Asn Met Glu
                405                 410                 415
```

-continued

```
Trp Asp Lys Ile Trp Ala Phe Asn Lys Lys Val Ile Asp Pro Val Ala
            420                 425                 430
Pro Arg Tyr Val Ala Leu Leu Lys Lys Glu Val Ile Pro Val Asn Val
        435                 440                 445
Pro Glu Ala Gln Glu Glu Met Lys Glu Val Ala Lys His Pro Lys Asn
465                 470                 475                 480
Pro Glu Val Gly Leu Lys Pro Val Trp Tyr Ser Pro Lys Val Phe Ile
465                 470                 475                 480
Glu Gly Ala Asp Ala Glu Thr Phe Ser Glu Gly Met Val Thr Phe
                485                 490                 495
Ile Asn Trp Gly Asn Leu Asn Ile Thr Lys Ile His Lys Asn Ala Asp
            500                 505                 510
Gly Lys Ile Ile Ser Leu Asp Ala Lys Phe Asn Leu Glu Asn Lys Asp
        515                 520                 525
Tyr Lys Lys Thr Thr Lys Val Thr Trp Leu Ala Glu Thr Thr His Ala
    530                 535                 540
Leu Pro Ile Pro Val Ile Cys Val Thr Tyr Glu His Leu Ile Thr Lys
545                 550                 555                 560
Pro Val Leu Gly Lys Asp Glu Asp Phe Lys Gln Tyr Val Asn Lys Asn
            565                 570                 575
Ser Lys His Glu Glu Leu Met Leu Gly Asp Pro Cys Leu Lys Asp Leu
        580                 585                 590
Lys Lys Gly Asp Ile Ile Gln Leu Gln Arg Arg Gly Phe Phe Ile Cys
    595                 600                 605
Asp Gln Pro Tyr Glu Pro Val Ser Pro Tyr Ser Cys Lys Glu Ala Pro
610                 615                 620
Cys Val Leu Ile Tyr Ile Pro Asp Gly His Thr Lys Glu Met Pro Thr
625                 630                 635                 640
Ser Gly Ser Lys Glu Lys Thr Lys Val Glu Ala Thr Lys Asn Glu Thr
            645                 650                 655
Ser Ala Pro Phe Lys Glu Arg Pro Thr Pro Ser Leu Asn Asn Asn Cys
        660                 665                 670
Thr Thr Ser Glu Asp Ser Leu Val Leu Tyr Asn Arg Val Ala Val Gln
    675                 680                 685
Gly Asp Val Val Arg Glu Leu Lys Ala Lys Lys Ala Pro Lys Glu Asp
690                 695                 700
Val Asp Ala Ala Val Lys Gln Leu Leu Ser Leu Lys Ala Glu Tyr Lys
705                 710                 715                 720
Glu Lys Thr Gly Gln Glu Tyr Lys Pro Gly Asn Pro Ala Glu Ile
            725                 730                 735
Gly Gln Asn Ile Ser Ser Asn Ser Ser Ala Ser Ile Leu Glu Ser Lys
        740                 745                 750
Ser Leu Tyr Asp Glu Val Ala Ala Gln Gly Glu Val Val Arg Lys Leu
    755                 760                 765
Lys Ala Glu Lys Ser Pro Lys Ala Lys Ile Asn Glu Ala Val Glu Cys
770                 775                 780
Leu Leu Ser Leu Lys Ala Gln Tyr Lys Glu Lys Thr Gly Lys Glu Tyr
785                 790                 795                 800
Ile Pro Gly Gln Pro Pro Leu Ser Gln Ser Ser Asp Ser Ser Pro Thr
            805                 810                 815
Arg Asn Ser Glu Pro Ala Gly Leu Glu Thr Pro Glu Ala Lys Val Leu
        820                 825                 830
```

-continued

Phe Asp Lys Val Ala Ser Gln Gly Glu Val Arg Lys Leu Lys Thr
    835                 840                 845

Glu Lys Ala Pro Lys Asp Gln Val Asp Ile Ala Val Gln Glu Leu Leu
850                 855                 860

Gln Leu Lys Ala Gln Tyr Lys Ser Leu Ile Gly Val Glu Tyr Lys Pro
865                 870                 875                 880

Val Ser Ala Thr Gly Ala Glu Asp Lys Asp Lys Lys Lys Glu Lys
                885                 890                 895

Glu Asn Lys Ser Glu Lys Gln Asn Lys Pro Gln Lys Gln Asn Asp Gly
            900                 905                 910

Gln Arg Lys Asp Pro Ser Lys Asn Gln Gly Gly Leu Ser Ser Ser
            915                 920                 925

Gly Ala Gly Glu Gly Gln Gly Pro Lys Lys Gln Thr Arg Leu Gly Leu
    930                 935                 940

Glu Ala Lys Lys Glu Glu Asn Leu Ala Asp Trp Tyr Ser Gln Val Ile
945                 950                 955                 960

Thr Lys Ser Glu Met Ile Glu Tyr His Asp Ile Ser Gly Cys Tyr Ile
                965                 970                 975

Leu Arg Pro Trp Ala Tyr Ala Ile Trp Glu Ala Ile Lys Asp Phe Phe
            980                 985                 990

Asp Ala Glu Ile Lys Lys Leu Gly Val Glu Asn Cys Tyr Phe Pro Met
        995                 1000                1005

Phe Val Ser Gln Ser Ala Leu Glu Lys Glu Lys Thr His Val Ala Asp
    1010                1015                1020

Phe Ala Pro Glu Val Ala Trp Val Thr Arg Ser Gly Lys Thr Glu Leu
1025                1030                1035                1040

Ala Glu Pro Ile Ala Ile Arg Pro Thr Ser Glu Thr Val Met Tyr Pro
            1045                1050                1055

Ala Tyr Ala Lys Trp Val Gln Ser His Arg Asp Leu Pro Ile Lys Leu
            1060                1065                1070

Asn Gln Trp Cys Asn Val Val Arg Trp Glu Phe Lys His Pro Gln Pro
        1075                1080                1085

Phe Leu Arg Thr Arg Glu Phe Leu Trp Gln Glu Gly His Ser Ala Phe
    1090                1095                1100

Ala Thr Met Glu Glu Ala Ala Glu Glu Val Leu Gln Ile Leu Asp Leu
1105                1110                1115                1120

Tyr Ala Gln Val Tyr Glu Glu Leu Leu Ala Ile Pro Val Val Lys Gly
            1125                1130                1135

Arg Lys Thr Glu Lys Glu Lys Phe Ala Gly Gly Asp Tyr Thr Thr Thr
            1140                1145                1150

Ile Glu Ala Phe Ile Ser Ala Ser Gly Arg Ala Ile Gln Gly Gly Thr
    1155                1160                1165

Ser His His Leu Gly Gln Asn Phe Ser Lys Met Phe Glu Ile Val Phe
    1170                1175                1180

Glu Asp Pro Lys Ile Pro Gly Glu Lys Gln Phe Ala Tyr Gln Asn Ser
1185                1190                1195                1200

Trp Gly Leu Thr Thr Arg Thr Ile Gly Val Met Thr Met Val His Gly
            1205                1210                1215

Asp Asn Met Gly Leu Val Leu Pro Pro Arg Val Ala Cys Val Gln Val
            1220                1225                1230

Val Ile Ile Pro Cys Gly Ile Thr Asn Ala Leu Ser Glu Glu Asp Lys
    1235                1240                1245

Glu Ala Leu Ile Ala Lys Cys Asn Asp Tyr Arg Arg Arg Leu Leu Ser

-continued

```
        1250                1255                1260
Val Asn Ile Arg Val Arg Ala Asp Leu Arg Asp Asn Tyr Ser Pro Gly
1265                1270                1275                1280
Trp Lys Phe Asn His Trp Glu Leu Lys Gly Val Pro Ile Arg Leu Glu
                1285                1290                1295
Val Gly Pro Arg Asp Met Lys Ser Cys Gln Phe Val Ala Val Arg Arg
                1300                1305                1310
Asp Thr Gly Glu Lys Leu Thr Val Ala Glu Asn Glu Ala Glu Thr Lys
            1315                1320                1325
Leu Gln Ala Ile Leu Glu Asp Ile Gln Val Thr Leu Phe Thr Arg Ala
    1330                1335                1340
Ser Glu Asp Leu Lys Thr His Met Val Val Ala Asn Thr Met Glu Asp
1345                1350                1355                1360
Phe Gln Lys Ile Leu Asp Ser Gly Lys Ile Val Gln Ile Pro Phe Cys
                1365                1370                1375
Gly Glu Ile Asp Cys Glu Asp Trp Ile Lys Lys Thr Thr Ala Arg Asp
                1380                1385                1390
Gln Asp Leu Glu Pro Gly Ala Pro Ser Met Gly Ala Lys Ser Leu Cys
            1395                1400                1405
Ile Pro Phe Lys Pro Leu Cys Glu Leu Gln Pro Gly Ala Lys Cys Val
    1410                1415                1420
Cys Gly Lys Asn Pro Ala Lys Tyr Tyr Thr Leu Phe Gly Arg Ser Tyr
1425                1430                1435                1440
```